US012797529B2

(12) United States Patent
Testani et al.

(10) Patent No.: US 12,797,529 B2
(45) Date of Patent: Nov. 17, 2026

(54) METHODS FOR DIRECT SODIUM REMOVAL IN PATIENTS HAVING HEART FAILURE AND RENAL DYSFUNCTION

(71) Applicant: DSRCo BV, Ghent (BE)

(72) Inventors: Jeffrey Testani, Guilford, CT (US); Ian Crosbie, London (GB); Oliver Goedje, Strasslach (DE)

(73) Assignee: DSRCo BV, Ghent (BE)

( * ) Notice: Subject to any disclaimer, the term of this patent is extended or adjusted under 35 U.S.C. 154(b) by 69 days.

(21) Appl. No.: 18/322,436

(22) Filed: May 23, 2023

(65) Prior Publication Data

US 2024/0390566 A1 Nov. 28, 2024

Related U.S. Application Data

(60) Provisional application No. 63/487,863, filed on Mar. 1, 2023.

(51) Int. Cl.
*A61M 1/28* (2006.01)
*A61K 31/7004* (2006.01)
*A61K 31/716* (2006.01)

(52) U.S. Cl.
CPC ......... *A61M 1/287* (2013.01); *A61K 31/7004* (2013.01); *A61K 31/716* (2013.01); *A61M 1/282* (2014.02)

(58) Field of Classification Search
CPC ............................................... A61M 1/28–288
See application file for complete search history.

(56) References Cited

U.S. PATENT DOCUMENTS

| | | | |
|---|---|---|---|
| 3,233,610 A | 2/1966 | Charles et al. |
| 3,516,410 A | 6/1970 | Hakim et al. |
| 3,540,451 A | 11/1970 | Zeman et al. |
| 3,575,158 A | 4/1971 | Summers |

(Continued)

FOREIGN PATENT DOCUMENTS

| | | |
|---|---|---|
| CN | 101291634 A | 10/2008 |
| CN | 101485683 A | 7/2009 |

(Continued)

OTHER PUBLICATIONS

Wolfson, M., Piraino, B., Hamburger, R. J., & Morton, A. R. (2002). A randomized controlled trial to evaluate the efficacy and safety of icodextrin in peritoneal dialysis. In American Journal of Kidney Diseases (vol. 40, Issue 5, pp. 1055-1065). Elsevier BV. https://doi.org/10.1053/ajkd.2002.36344 (Year: 2002).*

(Continued)

*Primary Examiner* — Courtney Fredrickson
(74) *Attorney, Agent, or Firm* — Greenberg Traurig, LLP; Christopher C. Bolten; Micheal L. Hebert

(57) ABSTRACT

Direct sodium removal ("DSR") therapy methods are provided for removing sodium and reducing fluid overload in patients with renal failure or heart failure, in which a patient has at least first and second DSR treatments with an infusate comprising 15-40 wt % icodextrin and up to 15 wt % dextrose that is instilled into a patient's peritoneal cavity for dwell period to cause sodium and excess fluid to migrate to the patient's peritoneal cavity, after which the infusate, sodium and ultrafiltrate is removed from the peritoneal cavity.

20 Claims, 7 Drawing Sheets

(56) References Cited

U.S. PATENT DOCUMENTS

| | | | |
|---|---|---|---|
| 3,608,088 | A | 9/1971 | Dorman et al. |
| 3,626,950 | A | 12/1971 | Schulte |
| 3,642,004 | A | 2/1972 | Osthagen et al. |
| 3,654,932 | A | 4/1972 | Newkirk et al. |
| 3,669,116 | A | 6/1972 | Heyer |
| 3,810,259 | A | 5/1974 | Summers |
| 3,910,283 | A | 10/1975 | Leveen |
| 4,014,346 | A | 3/1977 | Brownlee et al. |
| 4,083,786 | A | 4/1978 | Tsuda et al. |
| 4,240,434 | A | 12/1980 | Newkirk |
| 4,261,341 | A | 4/1981 | Hakim et al. |
| 4,347,543 | A | 8/1982 | Frister et al. |
| 4,354,933 | A | 10/1982 | Lester |
| 4,368,737 | A | 1/1983 | Ash |
| 4,398,910 | A | 8/1983 | Blake et al. |
| 4,416,657 | A | 11/1983 | Berglund |
| 4,418,693 | A | 12/1983 | LeVeen et al. |
| 4,419,094 | A | 12/1983 | Patel |
| 4,465,481 | A | 8/1984 | Blake |
| 4,468,219 | A | 8/1984 | George et al. |
| 4,475,898 | A | 10/1984 | Brodner et al. |
| 4,475,899 | A | 10/1984 | Muller |
| 4,490,137 | A | 12/1984 | Moukheibir |
| 4,553,956 | A | 11/1985 | Muller |
| 4,557,724 | A | 12/1985 | Gregonis et al. |
| 4,584,994 | A | 4/1986 | Bamberger et al. |
| 4,594,631 | A | 6/1986 | Iwaki |
| 4,595,390 | A | 6/1986 | Hakim et al. |
| 4,610,625 | A | 9/1986 | Bunn |
| 4,610,658 | A | 9/1986 | Buchwald et al. |
| 4,615,691 | A | 10/1986 | Hakim et al. |
| 4,618,343 | A | 10/1986 | Polaschegg |
| 4,632,435 | A | 12/1986 | Polyak |
| 4,650,463 | A | 3/1987 | LeVeen et al. |
| 4,657,530 | A | 4/1987 | Buchwald et al. |
| 4,687,471 | A | 8/1987 | Twardowski et al. |
| 4,690,673 | A | 9/1987 | Bloomquist |
| 4,725,207 | A | 2/1988 | Buchwald et al. |
| 4,772,257 | A | 9/1988 | Hakim et al. |
| 4,779,614 | A | 10/1988 | Moise |
| 4,784,638 | A | 11/1988 | Ghajar et al. |
| 4,850,955 | A | 7/1989 | Newkirk |
| D303,840 | S | 10/1989 | Weilbacher |
| 4,880,414 | A | 11/1989 | Whipple |
| 4,886,789 | A | 12/1989 | Milner |
| 4,904,236 | A | 2/1990 | Redmond et al. |
| 4,950,232 | A | 8/1990 | Ruzicka et al. |
| 4,963,129 | A | 10/1990 | Rusch |
| 4,963,133 | A | 10/1990 | Whipple |
| 4,991,594 | A | 2/1991 | Angelchik |
| 5,011,472 | A | 4/1991 | Aebischer et al. |
| 5,021,048 | A | 6/1991 | Buckholtz |
| 5,037,385 | A | 8/1991 | O'Byrne |
| 5,045,057 | A | 9/1991 | Van Driessche et al. |
| 5,057,075 | A | 10/1991 | Moncrief et al. |
| 5,071,408 | A | 12/1991 | Ahmed |
| 5,078,688 | A | 1/1992 | Lobodzinski et al. |
| 5,141,493 | A | 8/1992 | Jacobsen et al. |
| 5,147,281 | A | 9/1992 | Thornton et al. |
| 5,167,615 | A | 12/1992 | East et al. |
| 5,180,387 | A | 1/1993 | Ghajar et al. |
| 5,254,084 | A | 10/1993 | Geary |
| 5,356,386 | A | 10/1994 | Goldberg et al. |
| 5,360,414 | A | 11/1994 | Yarger |
| 5,385,541 | A | 1/1995 | Kirsch et al. |
| 5,387,188 | A | 2/1995 | Watson |
| 5,387,192 | A | 2/1995 | Glantz et al. |
| 5,391,143 | A | 2/1995 | Kensey |
| 5,395,320 | A | 3/1995 | Padda et al. |
| 5,395,350 | A | 3/1995 | Summers |
| 5,397,354 | A | 3/1995 | Wilk et al. |
| 5,431,637 | A | 7/1995 | Okada et al. |
| 5,472,323 | A | 12/1995 | Hirabayashi et al. |
| 5,474,683 | A | 12/1995 | Bryant et al. |
| 5,489,276 | A | 2/1996 | Jamshidi |
| 5,520,632 | A | 5/1996 | Leveen et al. |
| 5,549,579 | A | 8/1996 | Batdorf et al. |
| 5,575,770 | A | 11/1996 | Melsky et al. |
| 5,589,197 | A | 12/1996 | Shockley et al. |
| 5,593,394 | A | 1/1997 | Kanesaka et al. |
| 5,629,025 | A | 5/1997 | Shockley et al. |
| 5,631,025 | A | 5/1997 | Shockley et al. |
| 5,637,083 | A | 6/1997 | Bertrand et al. |
| 5,676,670 | A | 10/1997 | Kim |
| 5,713,864 | A | 2/1998 | Verkaart |
| 5,725,506 | A | 3/1998 | Freeman et al. |
| 5,788,468 | A | 8/1998 | Dewa et al. |
| 5,830,172 | A | 11/1998 | Leveen et al. |
| 5,902,336 | A | 5/1999 | Mishkin |
| 5,944,684 | A | 8/1999 | Roberts et al. |
| 5,945,449 | A | 8/1999 | Purcell et al. |
| 5,947,911 | A | 9/1999 | Wong et al. |
| 5,980,478 | A | 11/1999 | Gorsuch et al. |
| 5,980,480 | A | 11/1999 | Rubenstein et al. |
| 5,989,207 | A | 11/1999 | Hughes |
| 6,007,511 | A | 12/1999 | Prywes |
| 6,017,355 | A | 1/2000 | Hessel et al. |
| D420,738 | S | 2/2000 | Carter et al. |
| 6,022,333 | A | 2/2000 | Kensey |
| 6,027,442 | A | 2/2000 | Von Iderstein |
| 6,042,569 | A | 3/2000 | Finch, Jr. et al. |
| 6,099,513 | A | 8/2000 | Spehalski |
| 6,132,405 | A | 10/2000 | Nilsson et al. |
| 6,132,415 | A | 10/2000 | Finch et al. |
| 6,146,354 | A | 11/2000 | Beil |
| 6,162,238 | A | 12/2000 | Kaplan et al. |
| 6,162,487 | A | 12/2000 | Darouiche |
| 6,193,684 | B1 | 2/2001 | Burbank et al. |
| 6,214,802 | B1 | 4/2001 | Nakamura et al. |
| 6,234,964 | B1 | 5/2001 | Iliff |
| 6,245,039 | B1 | 6/2001 | Brugger et al. |
| 6,248,726 | B1 | 6/2001 | Alsop et al. |
| 6,254,567 | B1 | 7/2001 | Treu et al. |
| 6,264,601 | B1 | 7/2001 | Jassawalla et al. |
| 6,264,625 | B1 | 7/2001 | Rubenstein et al. |
| 6,417,750 | B1 | 7/2002 | Sohn |
| 6,436,087 | B1 | 8/2002 | Lewis et al. |
| 6,478,789 | B1 | 11/2002 | Spehalski et al. |
| 6,533,733 | B1 | 3/2003 | Ericson et al. |
| 6,554,822 | B1 | 4/2003 | Holschneider et al. |
| 6,585,681 | B2 | 7/2003 | Brugger et al. |
| 6,613,095 | B1 | 9/2003 | Levin |
| 6,648,906 | B2 | 11/2003 | Lasheras et al. |
| 6,656,227 | B2 | 12/2003 | Levin |
| 6,689,085 | B1 | 2/2004 | Rubenstein et al. |
| 6,814,547 | B2 | 11/2004 | Childers et al. |
| 6,827,682 | B2 | 12/2004 | Bugge et al. |
| 6,845,267 | B2 | 1/2005 | Harrison et al. |
| 6,846,168 | B2 | 1/2005 | Davis et al. |
| 6,854,467 | B2 | 2/2005 | Boekstegers |
| 6,875,192 | B1 | 4/2005 | Saul et al. |
| 6,887,214 | B1 | 5/2005 | Levin et al. |
| 6,894,456 | B2 | 5/2005 | Tsukamoto et al. |
| 6,905,474 | B2 | 6/2005 | Borgesen |
| 6,911,014 | B2 | 6/2005 | Wentling et al. |
| 6,921,378 | B2 | 7/2005 | O'Keefe et al. |
| 6,926,691 | B2 | 8/2005 | Miethke |
| 6,939,111 | B2 | 9/2005 | Huitt et al. |
| 6,945,949 | B2 | 9/2005 | Wilk |
| 6,949,080 | B2 | 9/2005 | Wolf et al. |
| 6,953,481 | B2 | 10/2005 | Phelps et al. |
| 6,955,655 | B2 | 10/2005 | Burbank et al. |
| 6,960,179 | B2 | 11/2005 | Gura |
| 6,964,652 | B2 | 11/2005 | Guiles et al. |
| 6,966,889 | B2 | 11/2005 | Saab |
| 6,974,445 | B2 | 12/2005 | Stergiopulos |
| 6,976,973 | B1 | 12/2005 | Ruddell et al. |
| 6,979,351 | B2 | 12/2005 | Forsell et al. |
| 6,981,964 | B2 | 1/2006 | Rioux et al. |
| 6,986,752 | B2 | 1/2006 | McGuckin, Jr. et al. |
| 6,994,700 | B2 | 2/2006 | Elkins et al. |
| 7,011,095 | B2 | 3/2006 | Wolf et al. |
| 7,017,340 | B2 | 3/2006 | Chicky |
| 7,025,739 | B2 | 4/2006 | Saul |

(56) References Cited

U.S. PATENT DOCUMENTS

| | | | |
|---|---|---|---|
| 7,025,742 | B2 | 4/2006 | Rubenstein et al. |
| 7,063,679 | B2 | 6/2006 | Maguire et al. |
| 7,118,857 | B2 | 10/2006 | Martis et al. |
| 7,128,735 | B2 | 10/2006 | Weston |
| 7,169,303 | B2 | 1/2007 | Sullivan et al. |
| 7,195,608 | B2 | 3/2007 | Burnett |
| D558,338 | S | 12/2007 | Itoh |
| D558,341 | S | 12/2007 | Fujiwara et al. |
| D558,342 | S | 12/2007 | Fujiwara et al. |
| 7,311,690 | B2 | 12/2007 | Burnett |
| 7,335,179 | B2 | 2/2008 | Burnett |
| 7,379,885 | B1 | 5/2008 | Zakim |
| 7,419,483 | B2 | 9/2008 | Shehada |
| 7,544,301 | B2 | 6/2009 | Shah et al. |
| 7,621,886 | B2 | 11/2009 | Burnett |
| 7,670,332 | B2 | 3/2010 | O'Keefe et al. |
| 7,909,790 | B2 | 3/2011 | Burnett |
| 8,012,118 | B2 | 9/2011 | Curtin et al. |
| 8,041,419 | B2 | 10/2011 | Giftakis et al. |
| 8,202,248 | B2 | 6/2012 | Burnett et al. |
| 8,241,239 | B2 | 8/2012 | Solomon et al. |
| 8,394,048 | B2 | 3/2013 | Burnett |
| 8,398,577 | B2 | 3/2013 | Burnett |
| 8,517,973 | B2 | 8/2013 | Burnett |
| 8,585,635 | B2 | 11/2013 | Degen et al. |
| 8,600,517 | B2 | 12/2013 | Forsell |
| 8,612,013 | B2 | 12/2013 | Forsell |
| 8,641,659 | B2 | 2/2014 | Soykan et al. |
| 8,704,484 | B2 | 4/2014 | Rosik et al. |
| 8,771,221 | B2 | 7/2014 | Burnett |
| 8,882,699 | B2 | 11/2014 | Burnett |
| 8,961,448 | B2 | 2/2015 | Forsell |
| 8,965,523 | B2 | 2/2015 | Forsell |
| 8,992,456 | B1 | 3/2015 | Powell |
| 9,039,652 | B2 | 5/2015 | Degen et al. |
| 9,138,521 | B2 | 9/2015 | Solomon et al. |
| 9,138,523 | B2 | 9/2015 | Burnett et al. |
| 9,144,660 | B2 | 9/2015 | Degen |
| 9,149,613 | B2 | 10/2015 | Degen et al. |
| D743,542 | S | 11/2015 | Degen |
| D743,543 | S | 11/2015 | Degen |
| 9,339,636 | B1 | 5/2016 | Khan et al. |
| 9,381,301 | B2 | 7/2016 | Lattanzio et al. |
| 9,421,347 | B2 | 8/2016 | Burnett |
| 9,440,017 | B2 | 9/2016 | Rohde et al. |
| 9,577,459 | B2 | 2/2017 | Degen et al. |
| 9,673,527 | B2 | 6/2017 | Yoon et al. |
| 9,675,327 | B2 | 6/2017 | Johnson et al. |
| 9,694,165 | B2 | 7/2017 | Forsell |
| 9,808,634 | B2 | 11/2017 | Forsell |
| 9,913,968 | B2 | 3/2018 | Burnett |
| 9,956,336 | B2 | 5/2018 | Degen et al. |
| 10,252,037 | B2 | 4/2019 | Degen et al. |
| 10,363,353 | B2 | 7/2019 | Lo et al. |
| 10,398,824 | B2 | 9/2019 | Burnett et al. |
| 10,569,003 | B2 | 2/2020 | Degen et al. |
| 10,716,922 | B2 | 7/2020 | Degen et al. |
| 10,744,254 | B1 | 8/2020 | Lindo et al. |
| 10,769,244 | B2 | 9/2020 | Degen et al. |
| 10,806,344 | B2 | 10/2020 | Goetz |
| 10,898,631 | B2 | 1/2021 | Inhaber et al. |
| 10,918,778 | B2 | 2/2021 | Inhaber et al. |
| 10,964,417 | B2 | 3/2021 | Gassman et al. |
| 11,235,131 | B2 | 2/2022 | Degen et al. |
| 11,464,891 | B2 | 10/2022 | Crosbie et al. |
| 11,559,618 | B2 | 1/2023 | Testani et al. |
| 11,602,583 | B2 | 3/2023 | Inhaber et al. |
| 11,793,916 | B2 | 10/2023 | Degen et al. |
| 11,839,712 | B2 | 12/2023 | Burnett et al. |
| 11,844,890 | B2 | 12/2023 | Testani et al. |
| 11,854,697 | B2 | 12/2023 | Degen et al. |
| 12,496,384 | B2 | 12/2025 | Testani et al. |
| 12,623,011 | B2 | 5/2026 | Crosbie et al. |
| 2001/0025170 | A1 | 9/2001 | Paderni |
| 2001/0027289 | A1 | 10/2001 | Treu et al. |
| 2002/0013545 | A1 | 1/2002 | Soltanpour et al. |
| 2002/0022793 | A1 | 2/2002 | Bertrand et al. |
| 2002/0091352 | A1 | 7/2002 | McGuckin, Jr. et al. |
| 2002/0107467 | A1 | 8/2002 | Levin |
| 2002/0123715 | A1 | 9/2002 | Sorenson et al. |
| 2003/0004495 | A1 | 1/2003 | Saul |
| 2003/0114787 | A1 | 6/2003 | Gura |
| 2003/0114898 | A1 | 6/2003 | Von Arx et al. |
| 2003/0163079 | A1 | 8/2003 | Burnett |
| 2003/0171710 | A1 | 9/2003 | Bassuk et al. |
| 2003/0216677 | A1 | 11/2003 | Pan et al. |
| 2003/0217962 | A1 | 11/2003 | Childers et al. |
| 2003/0220606 | A1 | 11/2003 | Busby et al. |
| 2004/0018228 | A1 | 1/2004 | Fischell et al. |
| 2004/0049288 | A1 | 3/2004 | Levin |
| 2004/0060865 | A1 | 4/2004 | Callan et al. |
| 2004/0098113 | A1 | 5/2004 | Forsell et al. |
| 2004/0106205 | A1 | 6/2004 | Stevenson et al. |
| 2004/0121982 | A1 | 6/2004 | Martis et al. |
| 2004/0126775 | A1 | 7/2004 | Altieri et al. |
| 2004/0147871 | A1 | 7/2004 | Burnett |
| 2005/0036983 | A1 | 2/2005 | Simon et al. |
| 2005/0075700 | A1 | 4/2005 | Schommer et al. |
| 2005/0096582 | A1 | 5/2005 | Burnett |
| 2005/0119598 | A1 | 6/2005 | Callan et al. |
| 2005/0131340 | A1 | 6/2005 | Sorenson et al. |
| 2005/0273034 | A1 | 12/2005 | Burnett |
| 2005/0276868 | A1 | 12/2005 | Degreve et al. |
| 2006/0010014 | A1 | 1/2006 | Brown |
| 2006/0024200 | A1 | 2/2006 | Nishikiori et al. |
| 2006/0036208 | A1 | 2/2006 | Burnett |
| 2006/0058731 | A1 | 3/2006 | Burnett et al. |
| 2006/0094984 | A1 | 5/2006 | Wood et al. |
| 2007/0055197 | A1 | 3/2007 | Shakir |
| 2007/0106205 | A1 | 5/2007 | Connell et al. |
| 2007/0208323 | A1 | 9/2007 | Gregorich et al. |
| 2007/0228071 | A1 | 10/2007 | Kamen et al. |
| 2007/0233042 | A1 | 10/2007 | Moehle et al. |
| 2007/0255345 | A1 | 11/2007 | Krause |
| 2007/0299317 | A1 | 12/2007 | Hoyme et al. |
| 2008/0024294 | A1 | 1/2008 | Mazar |
| 2008/0108935 | A1 | 5/2008 | Nyhart, Jr. |
| 2008/0129486 | A1 | 6/2008 | Jeckelmann et al. |
| 2008/0154173 | A1 | 6/2008 | Burnett |
| 2008/0214983 | A1 | 9/2008 | Mauge et al. |
| 2008/0230450 | A1 | 9/2008 | Burbank et al. |
| 2009/0054874 | A1 | 2/2009 | Barron et al. |
| 2009/0062887 | A1 | 3/2009 | Mass et al. |
| 2009/0069642 | A1 | 3/2009 | Gao et al. |
| 2009/0171241 | A1 | 7/2009 | Garcia et al. |
| 2009/0198174 | A1 | 8/2009 | Childers et al. |
| 2009/0222065 | A1 | 9/2009 | Dlugos, Jr. et al. |
| 2009/0275805 | A1 | 11/2009 | Lane et al. |
| 2009/0275924 | A1 | 11/2009 | Lattanzio et al. |
| 2009/0304600 | A1 | 12/2009 | Shetty |
| 2009/0318844 | A1 | 12/2009 | Burnett |
| 2010/0010832 | A1 | 1/2010 | Boute et al. |
| 2010/0022902 | A1 | 1/2010 | Lee et al. |
| 2010/0114012 | A1 | 5/2010 | Sandford et al. |
| 2010/0185225 | A1 | 7/2010 | Albrecht et al. |
| 2010/0215375 | A1 | 8/2010 | Reams |
| 2010/0222846 | A1 | 9/2010 | Goetz |
| 2010/0234793 | A1 | 9/2010 | Dacey, Jr. et al. |
| 2010/0241052 | A1 | 9/2010 | Dacey, Jr. et al. |
| 2010/0249692 | A1 | 9/2010 | Dacey, Jr. et al. |
| 2010/0270970 | A1 | 10/2010 | Toya et al. |
| 2010/0312163 | A1 | 12/2010 | Forsell |
| 2010/0312164 | A1 | 12/2010 | Forsell |
| 2011/0025261 | A1 | 2/2011 | Bersenev |
| 2011/0034986 | A1 | 2/2011 | Chou et al. |
| 2011/0163714 | A1 | 7/2011 | Ettes et al. |
| 2011/0172545 | A1 | 7/2011 | Grudic et al. |
| 2011/0184339 | A1 | 7/2011 | Tan |
| 2011/0184340 | A1 | 7/2011 | Tan et al. |
| 2011/0202041 | A1 | 8/2011 | Forsell |
| 2011/0245665 | A1 | 10/2011 | Nentwick |
| 2011/0291613 | A1 | 12/2011 | Rosik et al. |
| 2012/0032522 | A1 | 2/2012 | Schatz et al. |
| 2012/0035255 | A1 | 2/2012 | Fanelli et al. |

(56) References Cited

U.S. PATENT DOCUMENTS

| | | | | |
|---|---|---|---|---|
| 2012/0041279 | A1 | 2/2012 | Freeman et al. | |
| 2012/0191152 | A1 | 7/2012 | Kameli | |
| 2012/0199151 | A1 | 8/2012 | Haile | |
| 2012/0209085 | A1 | 8/2012 | Degen et al. | |
| 2012/0209165 | A1 | 8/2012 | Degen et al. | |
| 2012/0235503 | A1 | 9/2012 | Kesler et al. | |
| 2012/0235634 | A1 | 9/2012 | Hall et al. | |
| 2012/0289881 | A1 | 11/2012 | Lyu et al. | |
| 2013/0138452 | A1 | 5/2013 | Cork et al. | |
| 2013/0187619 | A1 | 7/2013 | Dunipace | |
| 2013/0197428 | A1 | 8/2013 | Cruz | |
| 2013/0199998 | A1 | 8/2013 | Kelly et al. | |
| 2013/0211322 | A1 | 8/2013 | Degen et al. | |
| 2013/0289334 | A1 | 10/2013 | Badstibner et al. | |
| 2013/0303971 | A1 | 11/2013 | Budgett et al. | |
| 2013/0317476 | A1 | 11/2013 | Searle et al. | |
| 2014/0005743 | A1 | 1/2014 | Giuffrida et al. | |
| 2014/0012180 | A1* | 1/2014 | Levin | A61M 1/28 604/9 |
| 2014/0018727 | A1 | 1/2014 | Burbank et al. | |
| 2014/0066841 | A1 | 3/2014 | Degen et al. | |
| 2014/0074180 | A1 | 3/2014 | Heldman et al. | |
| 2014/0098627 | A1 | 4/2014 | Mochizuki et al. | |
| 2014/0121487 | A1 | 5/2014 | Faybishenko et al. | |
| 2014/0121590 | A1 | 5/2014 | Degen | |
| 2014/0158623 | A1 | 6/2014 | Pudil et al. | |
| 2014/0200481 | A1 | 7/2014 | Johnson et al. | |
| 2014/0213966 | A1 | 7/2014 | Ostapoff et al. | |
| 2014/0266022 | A1 | 9/2014 | Degen et al. | |
| 2014/0275727 | A1 | 9/2014 | Bonde et al. | |
| 2014/0275827 | A1 | 9/2014 | Gill et al. | |
| 2014/0330147 | A1 | 11/2014 | Ousdigian et al. | |
| 2015/0019257 | A1 | 1/2015 | Doyle et al. | |
| 2015/0088090 | A1 | 3/2015 | Macy, Jr. | |
| 2015/0250427 | A1* | 9/2015 | Soykan | A61B 5/08 600/323 |
| 2015/0342872 | A1 | 12/2015 | Williamson et al. | |
| 2016/0000984 | A1 | 1/2016 | Burnett et al. | |
| 2016/0022971 | A1 | 1/2016 | Degen et al. | |
| 2016/0087687 | A1 | 3/2016 | Kesler et al. | |
| 2016/0151553 | A1 | 6/2016 | Bonde | |
| 2016/0183819 | A1 | 6/2016 | Burnett et al. | |
| 2016/0303313 | A1 | 10/2016 | Burke et al. | |
| 2016/0331947 | A1 | 11/2016 | Burnett | |
| 2017/0079760 | A1 | 3/2017 | Newman et al. | |
| 2017/0128654 | A1 | 5/2017 | Feld | |
| 2017/0136221 | A1 | 5/2017 | Budgett et al. | |
| 2017/0173262 | A1 | 6/2017 | Veltz | |
| 2017/0216611 | A1 | 8/2017 | Yoder et al. | |
| 2017/0245794 | A1 | 8/2017 | Sharma et al. | |
| 2017/0281846 | A1 | 10/2017 | Manda et al. | |
| 2017/0281848 | A1 | 10/2017 | Axelsson et al. | |
| 2017/0304597 | A1 | 10/2017 | Forsell | |
| 2017/0312530 | A1 | 11/2017 | Schilling et al. | |
| 2018/0043079 | A1 | 2/2018 | Gerber et al. | |
| 2018/0056050 | A1 | 3/2018 | Degen et al. | |
| 2018/0060520 | A1 | 3/2018 | Degen et al. | |
| 2018/0093081 | A1 | 4/2018 | Forsell | |
| 2018/0126130 | A1 | 5/2018 | Nitzan et al. | |
| 2018/0243495 | A1 | 8/2018 | Degen et al. | |
| 2018/0338914 | A1* | 11/2018 | Inhaber | A61P 7/08 |
| 2018/0344917 | A1 | 12/2018 | Inhaber et al. | |
| 2019/0232029 | A1 | 8/2019 | Degen et al. | |
| 2020/0054813 | A1 | 2/2020 | Burnett et al. | |
| 2020/0160057 | A1 | 5/2020 | Roxas et al. | |
| 2020/0188569 | A1 | 6/2020 | Degen et al. | |
| 2021/0134431 | A1* | 5/2021 | Garcia | G16H 10/60 |
| 2021/0187179 | A1* | 6/2021 | Inhaber | A61M 1/28 |
| 2021/0244381 | A1 | 8/2021 | Sweeney et al. | |
| 2022/0126072 | A1 | 4/2022 | Crosbie et al. | |
| 2023/0001065 | A1 | 1/2023 | Wirth et al. | |

FOREIGN PATENT DOCUMENTS

| | | | | |
|---|---|---|---|---|
| CN | 102024090 | A | 4/2011 | |
| CN | 201930383 | U | 8/2011 | |
| CN | 104077464 | A | 10/2014 | |
| CN | 104994894 | A | 10/2015 | |
| EP | 0366389 | A2 | 5/1990 | |
| EP | 0980685 | A2 | 2/2000 | |
| EP | 1362605 | A1 | 11/2003 | |
| EP | 1517718 | A1 | 3/2005 | |
| EP | 1539294 | A1 | 6/2005 | |
| EP | 1517718 | B1 | 10/2010 | |
| EP | 2244662 | A1 | 11/2010 | |
| EP | 2244663 | A1 | 11/2010 | |
| EP | 2244667 | A1 | 11/2010 | |
| EP | 2244758 | A1 | 11/2010 | |
| EP | 2244759 | A1 | 11/2010 | |
| EP | 2244760 | A1 | 11/2010 | |
| EP | 1539294 | B1 | 1/2011 | |
| EP | 2676638 | A1 | 12/2013 | |
| EP | 2349473 | B1 | 12/2016 | |
| EP | 2676638 | B1 | 7/2017 | |
| EP | 3275505 | A1 | 1/2018 | |
| EP | 2054105 | B1 | 7/2018 | |
| GB | 2350794 | A | 12/2000 | |
| JP | S63143074 | A | 6/1988 | |
| JP | H04327857 | A | 11/1992 | |
| JP | H0956810 | A | 3/1997 | |
| JP | 2000072658 | A | 3/2000 | |
| JP | 2000510552 | A | 8/2000 | |
| JP | 2004513681 | A | 5/2004 | |
| JP | 2005171892 | A | 6/2005 | |
| JP | 2005534400 | A | 11/2005 | |
| JP | 2006507018 | A | 3/2006 | |
| JP | 2010527247 | A | 8/2010 | |
| WO | WO-9741799 | A1 | 11/1997 | |
| WO | WO-9816171 | A1 | 4/1998 | |
| WO | WO-9934116 | A1 | 7/1999 | |
| WO | WO-0057833 | A1 * | 10/2000 | A61J 1/2093 |
| WO | WO-0207596 | A1 | 1/2002 | |
| WO | WO-03072166 | A1 | 9/2003 | |
| WO | WO-2004012806 | A1 | 2/2004 | |
| WO | WO-2004105730 | A1 | 12/2004 | |
| WO | WO-2005018708 | A2 | 3/2005 | |
| WO | WO-2006023589 | A2 | 3/2006 | |
| WO | WO-2008055248 | A2 | 5/2008 | |
| WO | WO-2009091267 | A2 | 7/2009 | |
| WO | WO-2009096854 | A1 | 8/2009 | |
| WO | WO-2010077851 | A2 | 7/2010 | |
| WO | WO-2012078230 | A1 | 6/2012 | |
| WO | WO-2012112664 | A1 | 8/2012 | |
| WO | WO-2013122580 | A1 | 8/2013 | |
| WO | WO-2013166038 | A2 | 11/2013 | |
| WO | WO-2014064053 | A2 | 5/2014 | |
| WO | WO-2014140277 | A1 | 9/2014 | |
| WO | WO-2015082555 | A1 | 6/2015 | |
| WO | WO-2015108782 | A1 | 7/2015 | |
| WO | WO-2017034452 | A1 | 3/2017 | |
| WO | WO-2017176687 | A1 | 10/2017 | |
| WO | WO-2018037359 | A1 | 3/2018 | |
| WO | WO-2018065945 | A1 | 4/2018 | |
| WO | WO-2018215917 | A1 | 11/2018 | |

OTHER PUBLICATIONS

Bellot, et al., Automated Low Flow Pump System for the Treatment of Refractory Ascites: A Multi-Center Safety and Efficacy Study, Journal of Hepatology, 58(5):922-927 (2013).

Clinical Pharmacology and Biopharmaceutics Review, Center for Drug Evaluation and Research, Approval Package for: Application No. 21-321, Aug. 31, 2001.

Costanzo, et al., Early Ultrafiltration in Patients with Decompensated Heart Failure and Diuretic Resistance, J. Am. Coll. Cardiol., 46(11):2047-2051(2005).

Doty, et al., Effect of Increased Renal Venous Pressure on Renal Function, J. Trauma., 47(6):1000-1003 (1999).

Extended European Search Report dated May 7, 2021 in EP Patent Appl. Serial No. 20215794.7 (1531).

(56) References Cited

OTHER PUBLICATIONS

Extended European Search Report dated Jun. 6, 2012 in EP Patent Appl. Serial No. EP05786343.3, 6 pages (0330).
Extended European Search Report dated Sep. 18, 2019 in EP Patent Appl. Serial No. 19172235.4 (0831).
Extended European Search Report dated Sep. 14, 2011 in EP Patent Appl. Serial No. EP11172759.0, 6 pages (0231).
Extended European Search Report dated Sep. 26, 2011 in EP Patent Appl. Serial No. EP07844792.7, 6 pages (0730).
Francois, et al., Peritoneal Dialysis for Chronic Congestive Heart Failure, Blood Purif., 40(1):45-52 (2015).
Fukuda, et al., Survivin, a Cancer Target with an Emerging Role in Normal Adult Tissues, Mol. Cancer Ther., 5(5):1087-1098 (2006).
Hanson, et al., Sodium in the dermis colocates to glycosaminoglycan scaffold, with diminishment in type 2 diabetes mellitus, JCI Insight, 6(12):e145470 (2021).
Hecking, et al., Sodium Setpoint and Sodium Gradient: Influence on Plasma Sodium Change and Weight Gain, Am J. Nephrol, 33(1):39-48 (2011).
Houlberg, et al., Terminal Right Heart Failure Due to Complex Congenital Cardiac Disease Successfully Managed by Home Peritoneal Drainage, Cardiol. Young, 13: 568-570 (2003).
International Search Report & Written Opinion dated Jul. 3, 2012 in Int'l PCT Patent Appl No. PCT/US12/25212, 34 pages (0810).
International Search Report & Written Opinion dated Apr. 15, 2008 in Int'l PCT Patent Appl No. PCT/US07/83261, 6 pages (0710).
International Search Report & Written Opinion dated Sep. 28, 2005 in Int'l PCT Patent Appl No. PCT/US04/26781, 4 pages (0410).
International Search Report & Written Opinion dated Apr. 16, 2015 in Int'l PCT Patent Appl. No. PCT/US2015/010840 (1610).
International Search Report & Written Opinion dated Mar. 18, 2013 in Intl PCT Appl. No. PCT/US2012/025188 (0910).
International Search Report & Written Opinion dated Jan. 4, 2018 in Intl PCT Patent Appl. U.S. Appl. No. PCT/IB2017/055092 (1410).
International Search Report and Written Opinion dated Feb. 2, 2018 in Intl PCT Patent Appl. No. PCT/IB2017/055093 (1710).
International Search Report dated Jul. 17, 2003, PCT/US03/05145, 3 pages (0210).
International Search Report dated Sep. 16, 2008, in Intl PCT Patent Appl. No. PCT/US2005/029305, 4 pages (0310).
Int'l Search Report and Written Opinion dated Aug. 24, 2018 in Int'l PCT Patent Appl. Serial No. PCT/IB2018/053587 (1510).
Kennt., Intra-Abdominal Pressure and Renal Function: the Venous Side of the Road, PulmCCM, Critical Care, Gi and Nutrition, Jul. 14, 2016, accessed on line on Mar. 27, 2017 at http://pulmccm.org/main/2016/critical-care-review/intra-abdominal-pressur-e-renal-function/.
McCausland, et al., Dialysate Sodium, Serum Sodium and Mortality in Maintenance Hemodialysis, 27(4):1613-1618 (2012).
McKinnie, et al., Long-term Therapy for Heart Failure With Continuous Ambulatory Peritoneal Dialysis, Archives of Internal Medicine, 145(6):1128-9 (Jun. 1985).
Medtronic Reveal Linq™ LNQ11, Insertable Cardiac Monitor, Clinician Manual, 98 pages (2015).
Munoz, et al., Dialysate Sodium and Sodium Gradient in Maintenance Hemodialysis: a Neglected Sodium Restriction Approach? Nephrol Dial Transplant, 26(4):1281-1287 (2011).
Nakayama, et al., Clinical Effect of Low Na Concentration Dialysate (120mEq/L) for CAPD Patients, Abstracts of the XIII Annual CAPD Conference, Peritoneal Dialysis International, 13(Supplement 1), (1993).
Ortiz, et al., Long-Term Automated Peritoneal Dialysis in Patients with Refractory Congestive Heart Failure, Advances in Peritoneal Dialysis, 19:77-80 (2003).
PCT International Search Report and Written Opinion dated Aug. 19, 2014 in PCT Patent Application No. PCT/EP2014/055104 (1310).
Pharmacology Review(s), Center For Drug Evaluation and Research, Approval Package for: Application No. 21-321, Dec. 14, 2001.
Puttagunta, et al., Peritoneal Dialysis for Heart Failure, Peritoneal Dialysis International, 35(6):645-649 (2015).
Rao, et al., "First-in-Human Experience With Peritoneal Direct Sodium Removal Using A Zero-Sodium Solution," A New Candidate Therapy for Volume Overload, Circulation, vol. 141, 2020, pp. 1043-1053.
Rosenblit, et al., "Peritoneal-Urinary Drainage for Treatment of Refractory Ascites: A Pilot Study," Nov./Dec. 1998, Journal of Vascular and Interventional Radiology, 9(6):998-1005,(1998).
Rosenblum, et al., Conceptual Considerations for Device-Based Therapy in Acute Decompensated Heart Failure, *Circulation: Heart Failure*, 13(4):e006731 (Apr. 2020).
Ruhi, et al., Use of Peritoneal Ultrafiltration in the Elderly Refractory Congestive Heart Failure Patients, Int. Urol. And Nephrol., 44(3):963-969 (2012).
Second Written Opinion dated May 16, 2019 in Int'l PCT Patent Appl. No. PCT/IB2018/053587 (1510).
Smyth, Chris, Pump implant for Cancer Patients 'is a Game-Changer' for Thousands, the Times, Health News, Jan. 18, 2013 (p. 11).
Sort, et al., Effect of Intravenous Albumin on Renal Impairment and Mortality in Patients with Cirrhosis and Spontaneous Bacterial Peritonitis, The New England Journal of Medicine, 341(6):403-409 (Aug. 5, 1999).
Supplementary European Search Report dated Jun. 4, 2010 in EP Patent Appl. Serial No. EP03719316.6, 3 pages (0230).
Tan et al., The Evidence on the Effectiveness of Management for Malignant Pleural Effusion: A Systematic Review, European Journal of Cardio-thoracic Surgery 29, 2006 (pp. 829-838).
Toto R.D., "Leveraging the Peritoneal as a New Diuretic Strategy for Heart Failure," Circulation, vol. 141, 2020, pp. 1054-1056.
Toxicology Review, NDA No. 21-321, Aug. 2001.
Warren, et al., Management of Malignant Pleural Effusions Using the Pleurx Catheter, Ann. Thrac. Sur. 85, 2008, (pp. 1049-1055).
Www.medtronic.com/us-en/patients/treatments-therapies/fainting-heart-monit- or/reveal-linq-icm.html (May 2017) (Accessed Nov. 27, 2017).
Zepeda-Orozco, et al., Dialysis Disequilibrium Syndrome, Pediatr. Nephrol, 27:2205-2211 (2012).
U.S. Appl. No. 10/369,550 / U.S. Pat. No. 7,335,179, filed Feb. 21, 2003 / Feb. 26, 2008.
U.S. Appl. No. 10/700,863 / U.S. Pat. No. 7,311,690, filed Nov. 3, 2003 / Dec. 26, 2007.
U.S. Appl. No. 10/826,237 / U.S. Pat. No. 7,909,790, filed Apr. 17, 2004 / Mar. 22, 2011.
U.S. Appl. No. 10/922,478 / U.S. Pat. No. 8,202,248, filed Aug. 18, 2004 / Jun. 19, 2012.
U.S. Appl. No. 11/181,539 / U.S. Pat. No. 7,621,886, filed Jul. 13, 2005 / Nov. 24, 2009.
U.S. Appl. No. 11/198,079 / U.S. Pat. No. 7,195,608, filed Aug. 4, 2005 / Mar. 27, 2007.
U.S. Appl. No. 11/933,214 / U.S. Pat. No. 8,398,577, filed Oct. 31, 2007 / Mar. 19, 2013.
U.S. Appl. No. 12/014,696 / U.S. Pat. No. 8,394,048, filed Jan. 15, 2008 / Mar. 12, 2013.
U.S. Appl. No. 13/029,069 / U.S. Pat. No. 8,517,973, filed Feb. 16, 2011 / Aug. 27, 2013.
U.S. Appl. No. 13/397,498 / U.S. Pat. No. 8,585,635, filed Feb. 15, 2012 / Nov. 19, 2013.
U.S. Appl. No. 13/397,509 / U.S. Pat. No. 9,149,613, filed Feb. 15, 2012 / Oct. 6, 2015.
U.S. Appl. No. 13/397,523 / U.S. Pat. No. 9,039,652, filed Feb. 15, 2012 / May 26, 2015.
U.S. Appl. No. 13/473,516 / U.S. Pat. No. 9,138,523, filed May 16, 2012 / Sep. 22, 2015.
U.S. Appl. No. 13/665,543 / U.S. Pat. No. 9,144,660, filed Oct. 31, 2013 / Sep. 29, 2015.
U.S. Appl. No. 13/789,250 / U.S. Pat. No. 8,771,221, filed Mar. 7, 2013 / Jul. 8, 2014.
U.S. Appl. No. 13/831,642 / U.S. Pat. No. 9,577,459, filed Mar. 15, 2013 / Feb. 21, 2017.
U.S. Appl. No. 13/973,981 / U.S. Pat. No. 8,882,699, filed Aug. 22, 2013 / Nov. 11, 2014.

(56) References Cited

OTHER PUBLICATIONS

U.S. Appl. No. 13/973,984 / U.S. Pat. No. 9,421,347, filed Aug. 22, 2013 / Aug. 23, 2016.
U.S. Appl. No. 14/077,005 / U.S. Pat. No. 9,956,336, filed Nov. 11, 2013 / May 1, 2018.
U.S. Appl. No. 14/155,079 / U.S. Pat. No. 9,673,527, filed Jan. 14, 2014 / Jun. 13, 2017.
U.S. Appl. No. 14/856,447 / U.S. Pat. No. 10,398,824, filed Sep. 16, 2015 / Sep. 3, 2019.
U.S. Appl. No. 14/874,187 / U.S. Pat. No. 10,252,037, filed Oct. 2, 2015 / Apr. 9, 2019.
U.S. Appl. No. 15/220,812 / U.S. Pat. No. 9,913,968, filed Jul. 27, 2016 / Mar. 13, 2018.
U.S. Appl. No. 15/249,192 / U.S. Pat. No. 10,716,922, filed Aug. 26, 2016 / Jul. 21, 2020.
U.S. Appl. No. 15/684,479 / U.S. Pat. No. 10,769,244, filed Aug. 23, 2017 / Sep. 8, 2020.
U.S. Appl. No. 15/965,727 / U.S. Pat. No. 10,569,003, filed Apr. 27, 2018 Feb. 25, 2020.
U.S. Appl. No. 15/985,598 / U.S. Pat. No. 10,918,778, filed May 21, 2018 Feb. 16, 2021.
U.S. Appl. No. 15/985,617 / U.S. Pat. No. 10,898,631, filed May 21, 2018 Jan. 26, 2021.
U.S. Appl. No. 16/378,376 / U.S. Pat. No. 11,235,131, filed Apr. 8, 2019 Feb. 1, 2022.
U.S. Appl. No. 16/550,035, filed Aug. 23, 2019.
U.S. Appl. No. 16/784,106, filed Feb. 6, 2020.
U.S. Appl. No. 17/013,806, filed Sep. 7, 2020.
U.S. Appl. No. 17/174,855 / U.S. Pat. No. 11,602,583, filed Feb. 12, 2021 Mar. 14, 2023.
U.S. Appl. No. 17/646,858, filed Jan. 3, 2022.
U.S. Appl. No. 17/650,183 / U.S. Pat. No. 11,464,891, filed Feb. 7, 2022 Oct. 11, 2022.
U.S. Appl. No. 17/661,737 / U.S. Pat. No. 11,559,618, filed May 2, 2022 Jan. 23, 2023.
U.S. Appl. No. 17/930,064, filed Sep. 6, 2022.
U.S. Appl. No. 17/938,418, filed Oct. 6, 2022.
U.S. Appl. No. 18/157,741, filed Jan. 20, 2023.
International Search Report & Written Opinion dated Jan. 10, 2024 in Int'l PCT Patent Appl. Serial No. PCT/IB2023/058117 (2210).
International Search Report & Written Opinion dated Mar. 30, 2023 in Int'l PCT Patent Appl. Serial No. PCT/IB2022/062709 (2110).
International Search Report & Written Opinion dated Jun. 14, 2023 in Int'l PCT Patent Appl. No. PCT/IB2023/050999 (1810).
International Search Report & Written Opinion dated Jun. 27, 2023 in Int'l PCT Patent Appl. No. PCT/IB2023/054061 (2010).
International Search Report & Written Opinion dated Nov. 8, 2023 in Int'l PCT Patent Appl. Serial No. PCT/IB2023/058630 (1910).
Aanen et al., A detailed analysis of sodium removal by peritoneal dialysis: comparison with predictions from the three-pore model of membrane function, *Nephrol. Dial. Transplant.*, 20(6):1192-1200 (2005).
Chen et al., Low-dose dopamine or low-dose nesiritide in acute heart failure with renal dysfunction: the ROSE acute heart failure randomized trial. Multicenter Study Randomized Controlled Trial, *JAMA*, 310(23):2533-2543 (2013).
Cox et al., Loop diuretic resistance complicating acute heart failure, *Heart Fail. Rev.*, 25(1):133-145 (2020).
Damman et al., The kidney in heart failure: an update, *Eur. Heart J.*, 36(23):1437-1444 (2015).
Finkelstein et al., Superiority of icodextrin compared with 4.25% dextrose for peritoneal ultrafiltration, *J. Am. Soc. Nephrol.*, 16(2):546-554 (2005).
Fischbach et al., Increasing sodium removal on peritoneal dialysis: applying dialysis mechanics to the peritoneal dialysis prescription, *Kidney Int.*, 89(4):761-766 (2016).
Heidenreich et al., 2022 AHA/ACC/HFSA Guideline for the Management of Heart Failure: A Report of the American College of Cardiology/American Heart Association Joint Committee on Clinical Practice Guidelines, *J. Am. Coll. Cardiol.*, 79(17):e263-e421 (2022).
Hodson et al., Natriuretic Response Is Highly Variable and Associated With 6-Month Survival: Insights From the ROSE-AHF Trial, *JACC Heart Fail.*, 7(5):383-391 (2019).
Hollenberg, et al., 2019 ACC Expert Consensus Decision Pathway on Risk Assessment, Management and Clinical Trajectory of Patients Hospitalized With Heart Failure, *Journal of the American College of Cardiology*, 74(15):1966 (2019).
Mcdonagh et al., "2021 ESC Guidelines for the diagnosis and treatment of acute and chronic heart failure," *Eur. Heart J.*, 42(36):3599-3726 (2021).
Moberly et al., "Pharmacokinetics of icodextrin in peritoneal dialysis patients," *Kidney Int Suppl.*, (81):S23-33 (2002).
Morelle et al., "Mechanisms of Crystalloid versus Colloid Osmosis across the Peritoneal Membrane," *J. Am. Soc. Nephrol.*, 29(7):1875-1886 (2018).
Mullens et al. The use of diuretics in heart failure with congestion—a position statement from the Heart Failure Association of the European Society of Cardiology, *Eur. J. Heart Fail.* 21(2):137-155 (2019).
Neragi-Mianoab., Malignant Pleural Effusion, Current and Evolving Approaches for its Diagnosis and Management, Lung Cancer 54:1-9(2006).
Rao et al., "Natriuretic Equation to Predict Loop Diuretic Response in Patients With Heart Failure," *J Am Coll Cardiol.* 77(6):695-708 (2021).
Testani et al., "Loop diuretic efficiency: a metric of diuretic responsiveness with prognostic importance in acute decompensated heart failure," *Circ. Heart Fail.*, 7(2):261-270 (2014).
Verbrugge et al., "Altered Hemodynamics and End-Organ Damage in Heart Failure: Impact on the Lung and Kidney," *Circulation*, 142(10):998-1012 (2020).

* cited by examiner

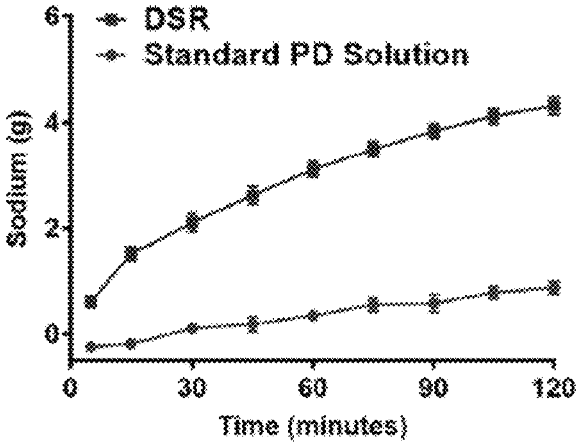
FIG. 2A
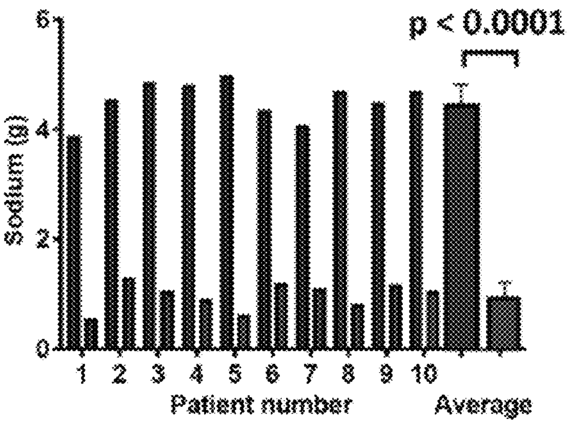
FIG. 2B
| Subject | Daily Dose | | | | Time since last DSR treatment (<D42) | Current Daily dose | Reduction |
|---|---|---|---|---|---|---|---|
| | At screening | During DSR treatment phase (D0 – D42) | At D43 | At D56 | | | |
| 101-001 | 80 | 0 | 0 | 0 | 12.5 months | 40 | -50% |
| 101-002 | 200 | 0 | 40 | 40 | 12.5 months | 80 | -60% |
| 101-003 | 400 | 0 | 40 | 40 | 10 months | 80 | -80% |
| 101-005 | 120 | 0 | 0 | 0 | 10.5 months | 40 E3D | [illegible] |
| 101-006* | 80 | 0 | 0 | 0 | 8.5 month | 20 2/W | [illegible] |
| 101-007* | 300 | 0 | 0 | 0 | 2 month | 40 TIW | [illegible] |
| 101-008* | 600 | 0 | 0 | 40 | 2 month | 80 | -87% |
| 101-009† | 800 | 0 | NA | NA | NA | NA | NA |
FIG. 3

| Subject | Dose | | Re-start time point after end phase 1 | Current time since end of ph 1 (Months) | Current reduction from screening |
|---|---|---|---|---|---|
| | at screening | at end ph 1 | | | |
| 01-01 | 400 | 0 | 20mg - 2.5m after ph 1<br>40mg - 5m after ph 1 | 15 | -90% |
| 01-03 | 160 | 0 | / | 13 | -100% |
| 01-04 | 200 | 0 | 20mg - 1m after ph 1 | 12 | -90% |
| 01-05 | 200 | 0 | / | 12 | -100% |
| 01-06 | 400 | 0 | / | 10 | -100% |
| 01-08 | 200 | 0 | 20mg - 5,5 m after ph 1 | 10 | -90% |
| 01-09 | 240 | 0 | 20mg - 0,5m after ph 1<br>40mg - 2m after ph 1<br>80mg - 3,5m after ph 1 | 9 | -67% |
| 01-10 | 800 | 0 | 13mg - 0,5m after ph 1<br>27mg - 2,5m after ph 1<br>40mg - 5m after ph 1 | 9 | -95% |
| 01-11 | 600 | 0 | 20mg - 1,25m after ph 1<br>40 mg - 4,5m after ph 1 | 6 | -93% |
| 01-12 | 400 | 0 | / | 6 | -100% |
| | | | | TOTAL | -93% |

METHODS FOR DIRECT SODIUM REMOVAL IN PATIENTS HAVING HEART FAILURE AND RENAL DYSFUNCTION

CROSS-REFERENCE TO RELATED APPLICATION

This application claims the benefit of priority of U.S. Provisional Patent Application No. 63/487,863, filed Mar. 1, 2023, the entire contents of which are incorporated by reference herein.

FIELD OF THE INVENTION

The present invention relates generally to methods of using infusates that are administered to a patient's peritoneal cavity to remove sodium and excess fluid from the body to alleviate fluid overload ("DSR therapy"). The above-incorporated patents describe such solutions for use in treating heart failure patients and patients having renal dysfunction. The inventions described herein are directed to specific protocols for conducting DSR therapy.

BACKGROUND

U.S. Pat. No. 10,918,778 B2 describes DSR infusates and methods of use for removing excess fluid by the removal of sodium from heart failure patients having residual renal function. In particular, the DSR infusates are specially formulated to be instilled into a patient's peritoneal cavity to remove sodium and water through one or both of: 1) ultrafiltration and/or 2) diffusion of sodium ions down a steep concentration gradient between the infusate instilled into patient's peritoneal cavity and surrounding tissues and vessels. After sodium and ultrafiltrate accumulates in the peritoneal cavity, it may be drained in accordance with conventional peritoneal dialysis methods, or more preferably, transferred by an implantable pump to the patient's urinary bladder, from which it is subsequently voided.

The foregoing patent describes that excess fluid is eliminated from the body to maintain a relatively stable serum sodium concentration, by one or both of: 1) inducing fluid to migrate from the patient's body into the peritoneal cavity, from where it is eliminated and/or 2) enhancing the excretion of excess water via the kidneys through urination. Patients suffering from heart failure are prone to accumulate additional sodium in body tissues and suffer from increased fluid retention. Similarly, patients suffering from kidney failure also are prone to accumulate additional sodium in body tissues and suffer from increased fluid retention.

U.S. Pat. No. 5,589,197 to Shockley et al. describes a dialysate for use in peritoneal dialysis, wherein the sodium concentration is between about 35 to 125 meq/L. As discussed in that patent, such solutions may be used to transport sodium to the peritoneal cavity for subsequent removal. Problems encountered with early experience with such low sodium dialysates, included symptomatic drops in blood pressure, and dialysis disequilibrium syndrome, a potentially fatal complication resulting in cerebral edema, coma and death. See, e.g., Nakayma, *Clinical Effect of Low Na Concentration Dialysate* (120 *mEq/L*) *for CAPD Patients*, PD Conference, San Sec, e.g., Zepeda-Orozco D, Quigley R., *Dialysis disequilibrium syndrome*, Pediatric Nephrology (Berlin, Germany) 2012; 27 (12): 2205-2211.

In accordance with existing standards of care, people with end-stage kidney disease generally undergo dialysis on a regular basis to remove metabolic toxins, and control sodium and fluid levels. The reported current average concentration of sodium in dialysate is generally about 132 mMol/L. Sec, e.g., Hecking M, Kainz A, Horl W H, Herkner H, Sunder-Plassmann G., *Sodium setpoint and sodium gradient: influence on plasma sodium change and weight gain. American Journal of Nephrology* 2011; 33 (1): 39-48; Mc Causland F R, Brunelli S M, Waikar S S., *Dialysate sodium, serum sodium and mortality in maintenance hemodialysis.* Nephrology Dialysis Transplantation 2012; 27 (4): 1613-8.

As reported in, e.g., Munoz Mendoza J, Sun S, Chertow G, Moran J, Doss S, Schiller B., *Dialysate sodium and sodium gradient in maintenance hemodialysis: a neglected sodium restriction approach*?, Nephrology Dialysis Transplantation 2011; 26 (4): 1281-7, experience with dialysate sodium concentrations higher than the patients' blood sodium levels show that such dialysates generally result in a net gain of sodium by the end of a dialysis session, which may result in increased fluid consumption and hypertension. Consequently, patients who undergo frequent hemodialysis sessions may experience chronic high sodium and fluid retention.

As described in the above-incorporated patents and applications, applicants have observed that eliminating fluid overload is a key clinical objective in managing heart failure and improving renal function in patients exhibiting renal dysfunction. Applicants have observed that achieving a stable reduction in fluid retention requires elimination of sodium from the body. Within certain ranges, patients having residual kidney function automatically will rebalance blood serum sodium concentration to maintain a constant serum osmolality and to maintain a stable sodium level, as described for example, in Guyton & Hall, Textbook of Medical Physiology. This is so because in patients with residual kidney function, the kidneys will remove excess water beyond that which might lead to hyponatremia.

It therefore would be desirable to develop methods of use in conducting DSR therapy for patients with fluid overload, such as patients having renal dysfunction or patients afflicted with heart failure. The desired DSR methods would assist such patients to achieve reductions in sodium and fluid overload not currently attainable with conventional dialysis techniques, while maintaining healthy serum sodium levels for such patients.

Accordingly, it would be desirable to provide methods of using DSR formulations, such as described in the above-incorporated patents and applications, and herein, to reduce fluid overload in patients suffering from renal dysfunction or heart failure.

SUMMARY OF THE INVENTION

In accordance with the present invention, methods of using DSR infusates are provided for removing sodium and reducing fluid overload in patients having heart failure, renal dysfunction or both, while aiding maintenance of stable serum sodium levels. Based on pre-clinical and clinical testing, the results of which are reported in the above-incorporated patents and applications and herein, applicants have observed that instilling low or no sodium dextrose infusates, or small volume infusates containing dextrose and icodextrin, into the peritoneal cavities of patients can significantly reduce symptoms and co-morbidities associated with fluid overload. For example, in applicants' early testing, DSR formulations comprising a sterile solution of dextrose in a range of 10 to 15 weight percent, with no or low sodium concentration, resulted in removal of significant amounts of sodium (e.g., up to 5 gm) and fluid (e.g., up to 1.7 liter) during a two-hour dwell time. Similarly, small volumes of infusates containing 10 wt % dextrose and 30 wt % icodextrin provided comparable results. Applicants observed in those tests that patients' blood serum sodium levels remained substantially constant. To the extent that the amount of sodium migrating to the patient's peritoneal cavity causes a transitory serum sodium imbalance, the patients' kidneys caused additional water to be excreted to rebalance the blood serum sodium level. Applicants theorize that if sodium migrates to, and is removed from, the peritoneal cavity, serum sodium levels will be maintained by elimination of free water via the kidneys and/or release into the blood of sodium stored extravascularly, e.g., within the interstitium of skin and skeletal muscle or alternative storage locations within the body.

In accordance with one aspect of the present invention, applicants theorize that the amounts of sodium and water removed during a specified dwell period will be function of the concentration of sodium in the infusate, the osmolality and oncotic force of the infusate, and the ability of constituents of the infusate to migrate across through the peritoneum and into the patient's tissue and vascular system. For example, is it expected that an infusate with little or no sodium will create a steep gradient that causes sodium to migrate to the peritoneal cavity, whereas an infusate with a sodium concentration approaching isomolar with blood serum levels, e.g., 130 meq/ml, will create a much shallower gradient. Thus, sodium ions will move to the fluid in the peritoneal cavity asymptotically until that gradient disappears and the sodium concentration in the fluid in the peritoneal cavity becomes isotonic, e.g., 135-150 meq/l, provided the dwell period is sufficiently long.

Similarly, the osmolality and oncotic force of the infusate will determine its ability to drive water to the peritoneal cavity, and will vary based on the constituent in the infusate and its ability to migrate across the peritoneum. For example, it is known that dextrose provides high osmolality when a dextrose-containing infusate is instilled into the peritoneal cavity. However, because the dextrose molecules quickly migrate/disappear from the peritoneal cavity, the ability of the infusate to drive ultrafiltrate to the peritoneal cavity declines fairly rapidly. By comparison, it is known that the oncotic force of an icodextrin solution is maintained because the icodextrin molecules do not pass readily across the peritoneum, resulting in a sustained movement of ultrafiltrate. Accordingly, the ability of the infusate to drive excess fluid into the patient's peritoneal cavity also will determine the ability of the DSR infusate to move excess sodium and water to the peritoneal cavity for subsequent removal. In addition, the more water that migrates to the peritoneal cavity, the greater the amount of sodium that will migrate to the peritoneal cavity to render peritoneal fluid isotonic for sodium ions. Further still, it has been observed that a mixture containing a high concentration of icodextrin and lower concentration of dextrose may be instilled in a relatively small volume, such as 500 ml, and result in a many fold volume of water and sodium migration to the peritoneal cavity.

In accordance with one aspect of the present invention, methods of using specific DSR formulations are provided for use with renal failure patients and heart failure patients to reduce fluid overload, dispense with the need for or improve the performance of loop diuretics, and extract extravascularly-stored excess sodium. In one preferred method, a DSR infusate is employed that comprising an aqueous solution of 15-40 wt % icodextrin and up to 15 wt % dextrose. More preferably, the DSR infusate has a low sodium concentration, e.g., <120 meq/l or is sodium-free.

Applicants have observed in feasibility trials that a single dose of 500 ml of a DSR infusate instilled into a patient's abdomen via a previously implanted peritoneal dialysis catheter for a 24 hour dwell period, and then drained via the peritoneal catheter, may have a beneficial result. Initial testing in ten human renal failure patients demonstrated that the patients did not experience significant abdominal pain or hemodynamic irregularities, and that serum sodium levels remained stable. About 2.5 L of fluid isotonic for sodium, i.e., 135-154 meq/l, was removed from each patient (net of the DSR infusate infused), demonstrating a ratio of about 1:5 for instilled infusate as compared to net drained fluid at completion of the dwell period. It is expected that these patients may undergo one or more conventional hemodialysis or peritoneal dialysis sessions during the follow-up period to remove blood-borne toxins. DSR treatment in those patients can be repeated on an as-needed basis more frequently as well.

In accordance with a further aspect of the present invention, a method of using specific DSR formulations is provided for use with renal failure and heart failure patients to reduce fluid overload, eliminate or reduce the need for loop diuretics, and extract extravascularly-stored excess sodium. In accordance with this method, a DSR comprises an aqueous solution of 15-40 wt % icodextrin and 0-15 wt % dextrose, and more preferably, has a low sodium concentration, e.g., <120 meq/l or is sodium-free. In use, an amount of between 125 ml and 1.0 liter of the DSR infusate periodically is infused into a patient's abdomen via an implanted peritoneal dialysis catheter for a period of 14 to 28 days. During this period, the DSR infusate may be instilled once a week or up to once daily, and retained in the peritoneal cavity for a 4-24 hour dwell period. Upon completion of the dwell period, the infusate and ultrafiltrate are drained via the peritoneal catheter. Following the 14-28 day treatment period, the peritoneal catheter is removed and the patient is observed during a follow-up period, e.g., 3-month. If needed, additional DSR treatments may conducted during the follow-up period, and lowered doses of loop diuretics, if any, may be administered. The patients may be observed for a further 9-month period to determine whether further treatment with loop diuretics, or an increase in loop diuretics dose, is warranted to avoid fluid overload, and if so when.

Applicants expect that, based on the initial test results for human renal failure patients discussed above, fluid drained from a patient's abdomen at conclusion of each 4 to 24 hour dwell period should be isotonic for sodium, with a ratio of about 1:4 to 1:5 for instilled infusate as compared to net drained amounts. Further, preliminary testing suggests that the heart failure patients treated with the above-described protocol may not need loop diuretics, or may require much lower doses of loop diuretics, for an extended follow-up period after the DSR treatment. That preliminary testing further indicates that patients exhibit improvement to cardiovascular and renal parameters following DSR treatment.

Methods of instilling and removing the DSR infusates of the present invention also are provided. In particular, the DSR infusates may be instilled into, and together with the ultrafiltrate removed from, the peritoneal cavity using conventional implanted peritoneal dialysis tubing sets. Alternatively, an external pump may be used to instill infusate into the peritoneal cavity via a subcutaneous port having a catheter that extends in the peritoneal cavity; the infusate and sodium-laden ultrafiltrate then may be extracted via the catheter and port at the conclusion of the dwell period. As a further alternative, removal of infusate and sodium-laden ultrafiltrate may be accomplished with an implantable pump system such as described in commonly-assigned U.S. Pat. No. 9,956,336, the contents of which are incorporated herein by reference. That patent describes a system for ambulatory peritoneal dialysis in which an infusate infused into a patient's peritoneal cavity is removed after a predetermined time and/or at predetermined intervals via an implantable pump that transfers fluid accumulated in the peritoneum to the patient's bladder, where it may be subsequently voided.

BRIEF DESCRIPTION OF THE DRAWINGS

Further features of the invention, its nature and various advantages will be more apparent from the accompanying drawings and the following detailed description of the preferred embodiments, in which:

FIGS. 2A and 2B are, respectively, graphs showing the amounts of sodium removed in a first in-human ("FIH") trial for 10 patients using a single dose of sodium-free 10 weight percent dextrose solution and a conventional peritoneal dialysis solution, sequentially administered via a conventional peritoneal dialysis catheter, as a function of dwell time, and sodium removal comparisons for each patient.

FIG. 3 is a table showing a durable effect post DSR-treatment for patients in a second study involving repeated DSR treatments, and who experienced a substantial reduction in need for diuretic drugs.

DETAILED DESCRIPTION OF THE INVENTION

Figure 1:
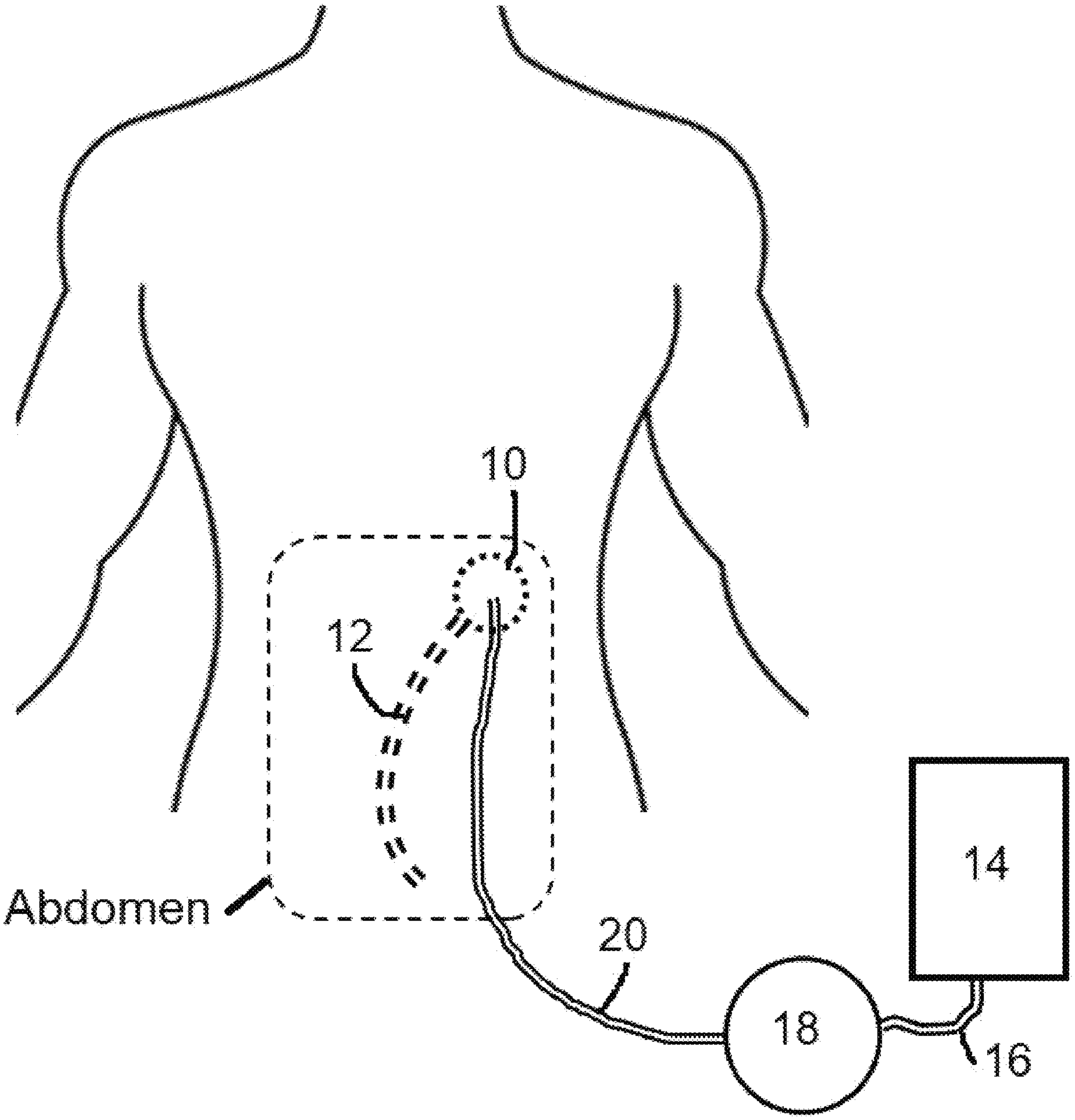
FIG. 1 is an exemplary system for instilling DSR infusate into, and extracting infusate and ultrafiltrate from, a patient's peritoneal cavity using a subcutaneous port coupled to a catheter that extends into the patient's peritoneal cavity.

The present invention is directed to infusate compositions and methods of treating fluid and/or sodium overload in patients with renal dysfunction, heart failure, or other disease associated with fluid overload. The infusate compositions and treatment methods are expected to be complimentary to conventional hemodialysis or peritoneal dialysis treatments and methods. Methods and compositions for treating heart failure patients suffering from fluid overload that have residual renal function are described in U.S. Pat. No. 10,918,778 B2, which is incorporated herein by reference in its entirety. The present invention is directed to specific methods for using DSR formulations to achieve significant, durable reduction in fluid overload and remove excess sodium. Based on preliminary data collected during first-in-man trials with exemplary DSR infusates, the methods and compositions of the present invention have been observed to improve sodium/fluid balance, reduce or even eliminate the need for loop diuretics, and improve parameters indicative of cardiovascular and renal health.

In accordance with one aspect of the present invention, a DSR infusate comprising an aqueous solution of up to 40 wt % icodextrin, and up to 15 wt % dextrose is instilled into a patient's peritoneal cavity using a peritoneal dialysis catheter, allowed to reside in the peritoneal cavity for a specified dwell period, and then drained via the peritoneal catheter.

Specific methods have been investigated for treating fluid overload in renal failure and heart failure patients. In one exemplary preferred method, use of loop diuretics may be reduced or discontinued. On a first treatment day of a 14 to 28 day treatment period, a patient has between 125 ml and 1 liter of DSR infusate, as described above, instilled into the peritoneal cavity via an implanted peritoneal catheter. The infusate remains in the peritoneal cavity for a 4-24 hour dwell period, and then is drained. During a second treatment day, which may be anywhere from immediately after the 4-24 hour dwell period is completed, up to one day, two days, three days, four days, five days, or six days later, the patient again has between 125 ml and 1 liter of DSR infusate, as described above, instilled into the peritoneal cavity via an implanted peritoneal catheter. After a 4-24 hour dwell period, the infusate and accumulated fluid is drained from the patient's peritoneal cavity. Subsequent treatment days during the 14 to 28 day treatment period may occur up to daily, i.e., up to between 14 to 28 daily treatments and 3 or 4 weekly treatments, each employing a 4-24 hour dwell. A three-month follow-up preferably is conducted for the patient, during which loop diuretics may be reduced or discontinued until fluid accumulation is observed to occur. If reduced doses or no loop diuretics are needed during the initial follow-up period, the patient may be observed for an additional nine month period, during which DSR treatment may be repeated. During this follow-up period, loop diuretics are prescribed at reduced dosages, or not at all, until the patient is observed to again begin accumulating fluid. DSR treatment also may be repeated during the nine month follow-up period.

Referring to FIG. 1, an exemplary alternative method, DSR fluid may be instilled and later withdrawn from the peritoneal cavity (outlined in dotted line) using subcutaneous port 10 coupled to catheter 12 that extends into the peritoneal cavity. DSR infusate may be pumped from bag or reservoir 14 to external pump 18 via line 16 and then delivered to subcutaneous port 10 via external catheter 20. As will be understood by one of ordinary skill in the art of medical devices, subcutaneous port 10 may include a self-healing membrane to allow a sharpened needle port of catheter 20 to removably be inserted into subcutaneous port 10. Catheter 20 may be withdrawn from subcutaneous port 10 during the dwell period. At the conclusion of the dwell period, catheter 20 may again be coupled to subcutaneous port 10, and external pump 18 used to evacuate the DSR infusate and ultrafiltrate from the patient's peritoneal cavity. As a further alternative, fluid may be removed from the peritoneal cavity using an implanted pump that transfers the fluid to the patient's bladder, such as the alfapump commercialized by Sequana Medical NV of Ghent, Belgium.

As used in this disclosure, a no or low sodium DSR infusate has a sodium content generally less than 120 meq/L and includes infusates having zero or only trace amounts of sodium. Applicants theorize that a DSR solution having large proportion of icodextrin, e.g. 30-40 wt %, may perform satisfactorily with a significant weight percentage of sodium, e.g., up to a sodium concentration isotonic with blood plasma. Additional studies to confirm this hypothesis are planned.

In one exemplary embodiment, the DSR therapy is conducted with a DSR infusate comprising a no or low sodium solution consisting of sterile water containing 0 to 15 weight percent dextrose and up to 40 weight percent icodextrin. Such an exemplary DSR infusate composition is expected to remove both sodium and water. More generally, formulations suitable for DSR therapy may contain from zero to 50 grams of dextrose per 100 ml of aqueous solution, and more preferably, 5 to 10 weight percent dextrose; from 0.5 to 50 grams of icodextrin per 100 ml of aqueous solution, and more preferably 15 to 30 weight percent icodextrin. Suitable DSR infusates also may employ high molecular weight biocompatible polymer solutions (weight average molecular weight Da>10,000) having from 0.5 to 50 grams of high molecular weight polymer per 100 ml of aqueous solution, and combinations thereof. Additional constituents that may be substituted for the dextrose and/icodextrin include solutions containing between 0.5 and 50 grams of one or more of: xylitol, glycerol, hyperbranched polyglycerol, sorbitol, carnitine, taurine, amino acids, urea, polyacrylate, polyethyleneimine, and stevioside per 100 ml aqueous solution. The aqueous solution contains at least purified water, and in addition may include electrolytes such as low amounts of magnesium or calcium salts, preservatives, ingredients having antimicrobial or antifungal properties, or buffering materials to control pH of the infusate. Icodextrin compositions generally may be preferable to dextrose compositions as icodextrin has been observed to experience a lower rate of uptake when employed in a peritoneal dialysis setting, and thus better preserves the peritoneal membrane compared to dextrose-based compositions.

The methods of using the DSR infusates optionally may include monitoring a patient's blood serum sodium level during a dwell period. For example, a blood sample may be taken during or after DSR therapy to monitor serum sodium level.

Feasibility Studies

The assignee of the present invention sought and obtained permission from investigational review boards to conduct a first trial to assess the feasibility of removing sodium from patients using a single dose of sodium-free 10% dextrose DSR solution, and two further studies with heart failure patients to assess safety and tolerance to serial DSR treatments. The first trial was conducted with ten patients with end-stage renal disease who regularly underwent peritoneal dialysis with previously implanted peritoneal catheters. In the second study, which was completed with seven heart failure patients, a sodium-free 10% dextrose DSR solution repeatedly was instilled via a subcutaneous port and after a dwell time, removed via an implantable pump. In a third study, which was completed on ten heart failure patients with persistent congestion, a sodium-free 10% dextrose DSR solution repeatedly was instilled via a subcutaneous port and after a dwell time, removed via an implantable pump. In all of these trials, a solution of 10 weight percent dextrose in sterile water was used as the DSR infusate. Details and results of these trials are described with respect to FIGS. 1 through 5.

In the first study, patients receiving peritoneal dialysis for end-stage renal disease with functioning peritoneal dialysis catheters underwent randomization and crossover to open-label DSR solution (sodium-free 10% dextrose) or standard peritoneal dialysis solution (Dianeal Low-Calcium with 4.25% dextrose; Baxter; Deerfield, IL), each separated by 1 week. This phase 1 study was conducted in patients receiving prevalent peritoneal dialysis rather than normal subjects to avoid the risk that placing a peritoneal dialysis catheter would pose to a normal subject. Inclusion criteria were the following: actively undergoing peritoneal dialysis with a functioning peritoneal dialysis catheter implanted less than 3 years, patient age greater than 18 years and judged by the treating nephrologist to be at or above optimal volume status (i.e., not dehydrated). Exclusion criteria were uncontrolled diabetes mellitus with frequent episodes of severe hyperglycemia; systolic blood pressure <100 mm Hg; serum sodium <130 mEq/L; one or more episodes of peritonitis in the previous 6 months or active infection of the peritoneal dialysis catheter; anemia with hemoglobin <8 g/dL; serum bicarbonate <18 mEq/L; anuric renal failure; inability to give written informed consent or to follow the study protocol; and pregnant or lactating.

A 4.25% dextrose peritoneal dialysis solution was selected as the comparison solution because it is the most effective marketed peritoneal dialysis solution for fluid/sodium removal and has an osmolarity similar to that of 10% dextrose. Before instillation of the study fluid, there was a 30-minute drain of the abdomen with the patient assuming multiple positions during this time to ensure as complete drainage as possible. Given that this was a dialysis population with a tendency to develop acidosis, all patients were given 30 mEq sodium citrate/citric acid by mouth. Next, 1 L of either DSR infusate or standard peritoneal dialysis solution was infused into the peritoneum and left to dwell for 2 hours. The intraperitoneal volume was determined longitudinally using the indicator dilution technique with I-131-radiolabeled albumin (Daxor Inc), in addition to direct measurement of drained fluid at the end of the dwell. Vital signs, blood (every 30 minutes), and peritoneal fluid (every 15 minutes) were obtained serially throughout the protocol. Patients in the DSR group were given 50% of the ultrafiltration volume back at the end of the dwell in the form of intravenous normal saline to replace sodium/volume losses. The primary end point was safety/tolerability, defined as completion of the 2-hour dwell without significant discomfort or adverse events. The secondary efficacy end point was the difference in sodium removal between the DSR solution and standard peritoneal dialysis solution.

Ten patients completed the crossover study. The baseline characteristics for these patients are presented in the Table below.

| Characteristics | All Patients |
|---|---|
| Demographics | |
| Age, y | 54 ± 12 |
| Male sex, n (%) | 70 (7) |
| White race, n (%) | 50 (5) |
| Comorbidities, n (%) | |
| Diabetes mellitus | 30 (3) |
| Hypertension | 90 (9) |
| Heart failure | 10 (1) |
| Physical examination | |
| Weight, lb, mean ± SD | 251 ± 72 |

-continued

| Characteristics | All Patients |
|---|---|
| SBP, mm Hg | 144 (132-156) |
| Peritoneal Dialysis variables | |
| Peritoneal Dialysis Catheter vintage, years | 1.3 ± 0.9 |
| Automated Peritoneal Dialysis use, n (%) | 100 (10) |
| icodextrin use, n (%) | 30 (3) |
| Last fill, n (%) | 40 (4) |
| Type of renal disease, n (%) | |
| Diabetic nephropathy | 2 (20) |
| Hypertensive nephrosclerosis | 1 (10) |
| Excessive NSAID use | |
| Systemic lupus erythematosus | |
| Nephrotic syndrome | |
| Immunoglobulin A nephropathy | |
| Granulomatosis with polyangitis-ESRD | |
| Polycystic kidney disease | |
| Failed allograft | |
| Medications, n (%) | |
| Antihypertensives | 90 (9) |
| Loop diuretics | 60 (6) |
| Calcium channel blockers | 60 (6) |
| β-Blockers | 50 (5) |
| ACE inhibitors | 30 (3) |
| Thiazide-type diuretics | 20 (2) |
| Angiotensin II receptor blockers | 20 (2) |
| α-Agonists | 10 (1) |
| Insulin | 20 (2) |
| Laboratory values, mean ± SD | |
| Sodium, mmol/L | 137.93.5 |
| Hemoglobin, g/dL | 10.21.3 |
| BUN, mmol/L | 5419 |
| Calcium, mmol/L | 1.11 ± 0.14 |
| Potassium, mmol/L | 4.2 ± 0.4 |

The primary end point, defined as completion of the 2-hour dwell without significant discomfort or adverse events, was met in all 10 patients. Overall, the treatment was well tolerated, with 2 of 10 patients reporting mild and short-duration cramping during instillation of the 10 wt % dextrose solution; one of those patients had similar cramping during the standard peritoneal dialysis solution instillation. There were no significant differences in blood pressure or peak heart rate between the 2 groups. Changes in plasma glucose were larger with the 10 wt % dextrose solution compared with standard peritoneal dialysis solution, with the most pronounced differences early in the dwell. However, differences in plasma glucose completely resolved after draining of the solution. No patients developed severe hyperglycemia at any time point in either group. The relative glucose absorption was the same between the 10 wt % dextrose and standard peritoneal dialysis solution; however, given the larger absolute amount of glucose in 10 wt % dextrose, the absolute quantity of glucose absorbed was larger with 10 wt % dextrose.

Serum sodium was not different between groups. Removal of off-target nonsodium electrolytes with DSR such as potassium (5.5±1.1 mmol), magnesium (1.7±2.5 mmol), phosphorus (1.9±0.6 mmol), and calcium (1.6±0.3 mmol) was negligible, and plasma electrolyte and chemistry parameters were stable throughout the dwell. As shown in FIG. 2A, the secondary efficacy outcome of superior sodium removal with sodium-free 10 wt % dextrose (4.5±0.4 g) compared with standard peritoneal dialysis solution (1.0±0.3 g) was met (P<0.001). In addition to a substantially higher average sodium clearance, the consistency of sodium removal was excellent. The absolute variability between individual patients' sodium removal and the average sodium removal was similar between DSR infusate and standard peritoneal dialysis solution, as depicted in FIG. 2B. However, because the total sodium removed in standard peritoneal dialysis solution was substantially lower, the relative variability between individuals was much higher with standard peritoneal dialysis solution, ranging from 8% to 75% of the average total sodium removal compared with 2% to 18% in patients receiving DSR infusate. Fluid removal was also greater with sodium-free 10 wt % dextrose, also with a high degree of consistency across patients.

The primary finding from the first human trial is that substantial sodium removal via the peritoneal membrane is feasible. In particular, it was observed that using 1 liter of sodium free 10 wt % dextrose solution, leveraged both diffusive and convective forces, and could remove >4 g sodium in 2 hours. The DSR therapy was well tolerated, with limited effect on plasma electrolyte levels, minimal off-target solute removal, and freedom from discomfort in the majority of human participants. The sodium removal was scalable, with substantially larger quantities of sodium removed by increasing the volume of 10 wt % dextrose cycled into the peritoneal space.

In the second study, the primary objective was to assess the safety and tolerability of serial treatment with DSR therapy in chronic stable diuretic resistant heart failure patients. A secondary objective of this study was to assess the impact of serial treatment with DSR therapy on parameters of cardiovascular and renal function, and diuretic response. In this study, DSR infusate was instilled into the patient's peritoneal cavities via subcutaneous port; seven patients completed the study. The implantable pump system developed by the assignee of the present application, Sequana Medical, N.V., was employed to move fluid from the patients' peritoneal cavities to their bladders. Patients were admitted into the second study, in accordance with the following criteria:

Inclusion Criteria:

1. eGFR>30 ml/min/14.73m2
2. Diagnosis of heart failure with one of the following:
   a. nt-proBNP>400 pg/ml (or BNP>100 pg/ml) and oral diuretic dose ≥80 mg furosemide equivalents OR
   b. Oral diuretic dose ≥120 mg furosemide equivalents
3. Stable diuretic dose for 30 days
4. Systolic blood pressure ≥100 mmHg
5. Determined by treating provider to be at optimal volume status Exclusion Criteria:

1. Serum sodium <135 mEq/L
2. Severe hyperkalemia or baseline plasma potassium >4.5 mEq/L
3. History of significant bladder dysfunction expected to interfere with ability of subject to tolerate DSR pumping into bladder
4. Uncontrolled diabetes with frequent hyperglycemia or Type 1 diabetes The second study ran for a total of 6 weeks, plus a two-week follow-up. After screening, eight patients were implanted with the Alfapump® implantable pump about two weeks prior to initiation of the trial. Three days before the DSR trial was begun, each patient was given an intravenous administration of 40 mg of furosemide, followed by a 6-hour timed urine collection. At the outset of the DSR trial, all loop diuretics were stopped. During the following two weeks, the patients were resident in-hospital with diets controlled at 3 grams of sodium per day for the first week and 5 grams of sodium the second week. Patients then were permitted to return home. During the two week in-hospital stay and the following four weeks, the patients underwent DSR sessions up to three times a week using a sodium-free 10 weight percent dextrose DSR solution. At the conclusion of the six weeks of DSR sessions, the patients again underwent a diuretic challenge with intravenous administration of 40 mg of furosemide, followed by a 6-hour timed urine collection.

Baseline characteristics for the group of seven patients that completed the study are set forth in the table below:

| N = 7 | Result | Min:Max |
|---|---|---|
| Age-Years (Mean ± SD) | 62.0 ± 8.5 | 49:77 |
| Male-% | 100 | N/A |
| Height-cm (Mean ± SD) | 172.1 ± 5.4 | 163:182 |
| Weight-kg (Mean ± SD) | 75.6 ± 17.7 | 53.0:107.8 |
| BMI-kg/$m^2$ (Mean ± SD) | 25.4 ± 4.8 | 19.3:32.6 |
| Ejection Fraction-% (Mean ± SD) | 25.0 ± 2.5 | 20:28 |
| Nt-proBNP-pg/mL (Mean ± SD) | 3982.9 ± 2594.9 | 1536:7853 |
| Serum creatinine-μmol/L (Mean ± SD) | 106.9 ± 37.2 | 62.2:190.4 |
| Hematocrit-% (Mean ± SD) | 45.5 ± 5.9 | 36.6:55.2 |
| Furosemide equivalents-mg (Mean ± SD) | 254.3 ± 179.1 | 80:600 |

By the conclusion of the six-week study, all patients had remained off loop diuretics for the entire period. A neutral sodium balance was achieved (−1.3 grams) during the 2 week in-hospital period. Stable weight over the duration of the study also was achieved (75.6 to 75.5 kg). Most patients had down titration of DSR therapy to maintain constant weight; the volume of 10 wt % dextrose DSR solution was on average 750±348 ml/treatment.

As shown in table below, by completion of the study, study participants experienced a significant reduction in measured N-terminal-pro B-type natriuretic peptide ("NT-proBNP") and creatinine levels, indicating improvement in cardio-renal function.

| Parameter | Pre-study | Post-study | Delta % |
|---|---|---|---|
| Nt-proBNP (pg/mL) (Mean ± SD) | 3982.9 ± 2594.9 | 2780 ± 1544.1 | −30.2 |
| Creatinine (μmol/L) (Mean ± SD) | 106.09 ± 37.20 | 82.24 ± 17.27 | −23.1 |
| Hematocrit-% (Mean ± SD) | 45.5 ± 5.9 | 43.40 ± 4.52 | −4.6 |
| Ejection Fraction-% (Mean ± SD) | 25.0 ± 2.5 | 26.43 ± 3.99 | +5.7 |
| Furosemide equivalents-mg (Mean ± SD) | 254.3 ± 179.1 | 11.43 ± 19.52 | −95.5 |
| Diuretic Challenge (40 mg furosemide)-6H urine out (ml) | 875.7 ± 281.1 | 1963.1 ± 464.6 | +124.2 |
| Diuretic Challenge (40 mg furosemide)-6H Na out (gr) | 1.85 ± 1.02 | 5.37 ± 1.27 | +190.0 |

Figure 4A:
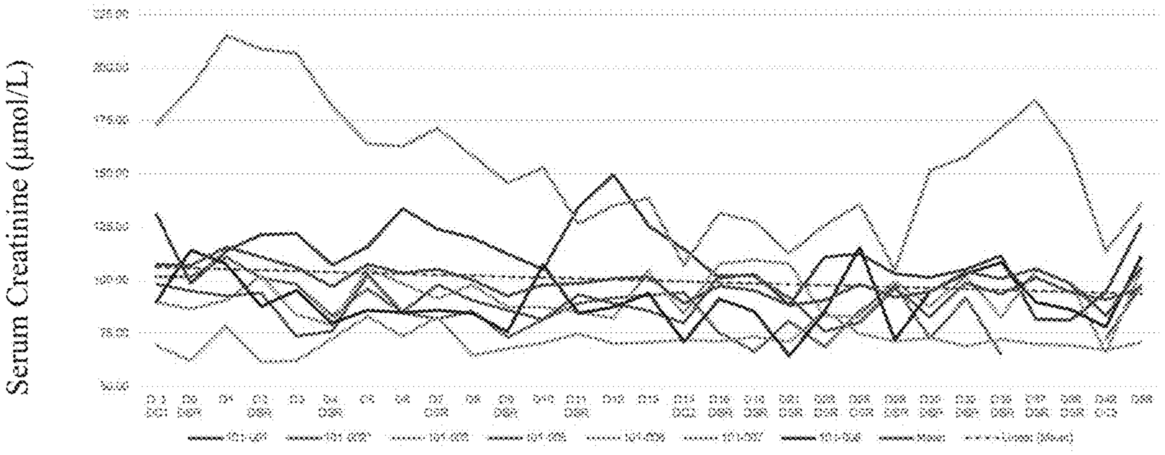
FIGS. 4A, 4B and 4C are, respectively, graphs showing the evolution of observed changes in physiologic parameters for 7 patients during the second human trial.
Figure 4B:
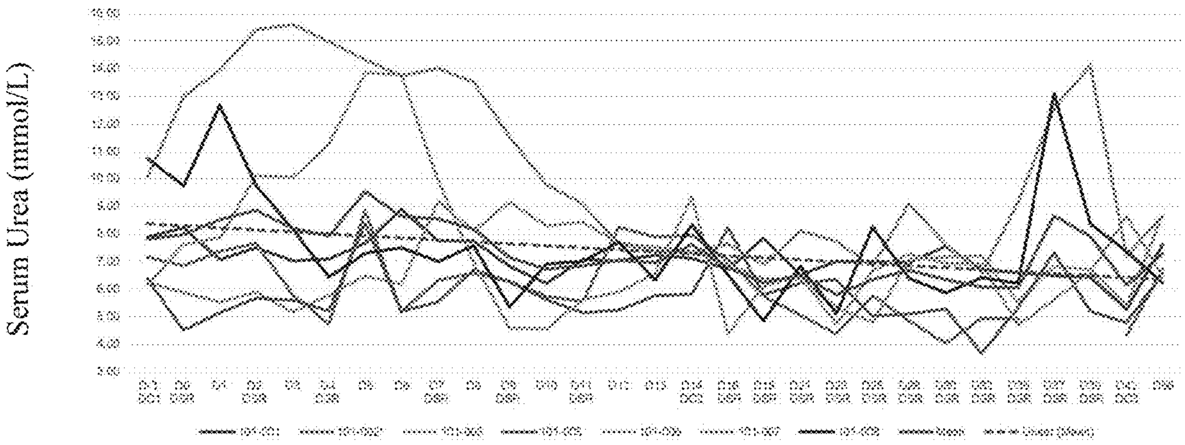
Figure 4C:
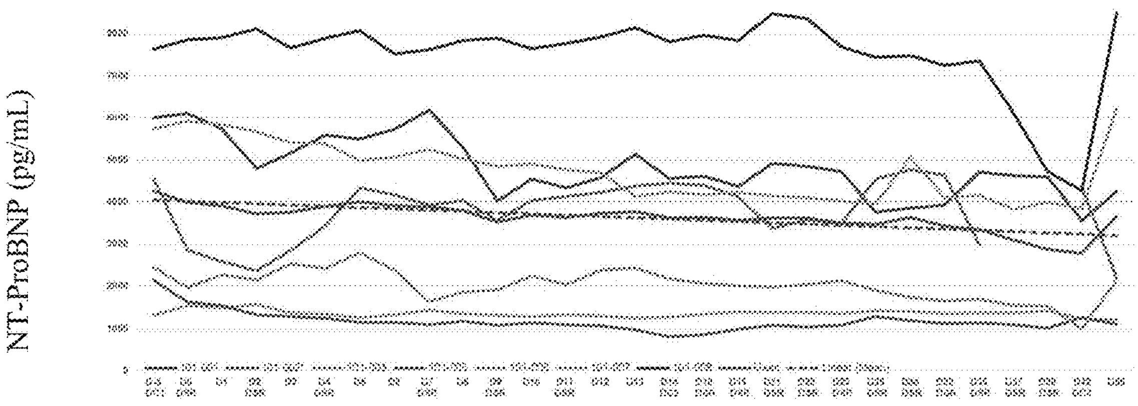

FIG. 3 is a table reporting the results of follow-up evaluations with seven of the study patients, and indicates that the effect of the DSR therapy in reducing diuretic resistance is durable, with patients experiencing a reduction between 94% and 50% of their daily diuretic dosing at 8 to 12 months following their last DSR session. FIGS. 4A, 4B and 4C depict the temporal trends of improvement for the study patients over the six-week period. This second human study demonstrated that six weeks of DSR therapy, using an implantable pump to remove the DSR solution and ultrafiltrate, was overall well tolerated and successfully maintained a neutral sodium balance and stable body weight, despite reduction of loop diuretics. The study also showed significant benefit to cardiovascular and renal function, as observed by meaningful improvement in NT-proBNP and renal function. In addition, diuretic resistance substantially and durably improved.

The third trial was conducted in which a sodium-free 10 wt % dextrose DSR infusate was used repeatedly in patients afflicted with heart failure and severe fluid overload. The primary objectives of this third study are to further demonstrate safety and tolerability of the Alfapump® DSR implant procedure and DSR therapy in subjects with residual congestion due to heart failure, while a secondary objective it so establish feasibility of the DSR infusate therapy to remove excess sodium and fluid to restore and maintain euvolemia without need for additional loop diuretic treatment.

The patient demographics for the third study are:

| Parameter | Result | Min:Max |
|---|---|---|
| Age-Years (Mean ± SD) | 64.4 ± 9.6 | 44:81 |
| Male | 10/10 (100%) | N/A |
| Weight-kg (Mean ± SD) | 82.9 ± 18.2 | 54.6:113.5 |
| Ejection Fraction-% (Mean ± SD) | 22.9 ± 3.8 | 18:28 |
| BMI-kg/$cm^2$ (Mean ± SD) | 28.3 ± 5.8 | 21:38 |
| Nt-proBNP-pg/mL (Mean ± SD) | 6628 ± 2483 | 2143:9000( * |
| Serum creatinine-μmol/L (Mean ± SD) | 141.7 ± 46.4 | 67.6:243.3 |
| eGFR-mL/min/1.73 $m^2$ (Mean ± SD) | 51.4 ± 23.4 | 23:110 |
| Furosemide equivalents-mg (Mean ± SD) | 360.0 ± 196.8 | 160:800 |

An initial phase of the third study called for intensive DSR treatments, up to daily, for a two week period, with loop diuretics administered pro re nata (as needed). If the patient responded to the initial two week period, he would enter a second phase of the study, during which DSR treatments would be conducted once monthly in a four month follow-up period. If the patient did not sufficiently respond to the initial two-week course of DSR treatments, a further course of intensive DSR treatments would be conducted, before the patient moved to the second phase consisting of once monthly DSR treatment in a four month follow-up period.

The table below presents the results obtained at the conclusion of two weeks of intensive DSR treatments. As shown in the table, all patients were able to reduce their need for loop diuretics to zero.

| Parameter | Pre-Study | Post-Phase 1 | Delta % |
|---|---|---|---|
| Diuretic Challenge (40 mg furosemide)-6H urine out (ml) (Mean ± SD) | 916.6 ± 219.6 | 1925.9 ± 512.9 | +110.1 |
| Diuretic Challenge (40 mg furosemide)-6H Na out (gr) (Mean ± SD) | 1.9 ± 0.8 | 4.9 ± 1.9 | +163.4 |
| Weight-kg (Mean ± SD) | 82.9 ± 18.2 | 76.3 ± 18.1 | −7.9 |
| Nt-proBNP (pg/mL) (Mean ± SD) | 6628 ± 2483 | 4118 ± 2401 | −37.8 |
| Creatinine (μmol/L) (Mean ± SD) | 141.7 ± 46.4 | 129.0 ± 36.0 | −9.0 |
| eGFR (mL/min/1.73 $m^2$) (Mean ± SD) | 51.4 ± 23.4 | 54.80 ± 16.9 | +6.6 |
| Furosemide equivalents-mg (Mean ± SD) | 360.0 ± 196.8 | 0.0 ± 0.0 | −100.0 |

Figures 5, 6:
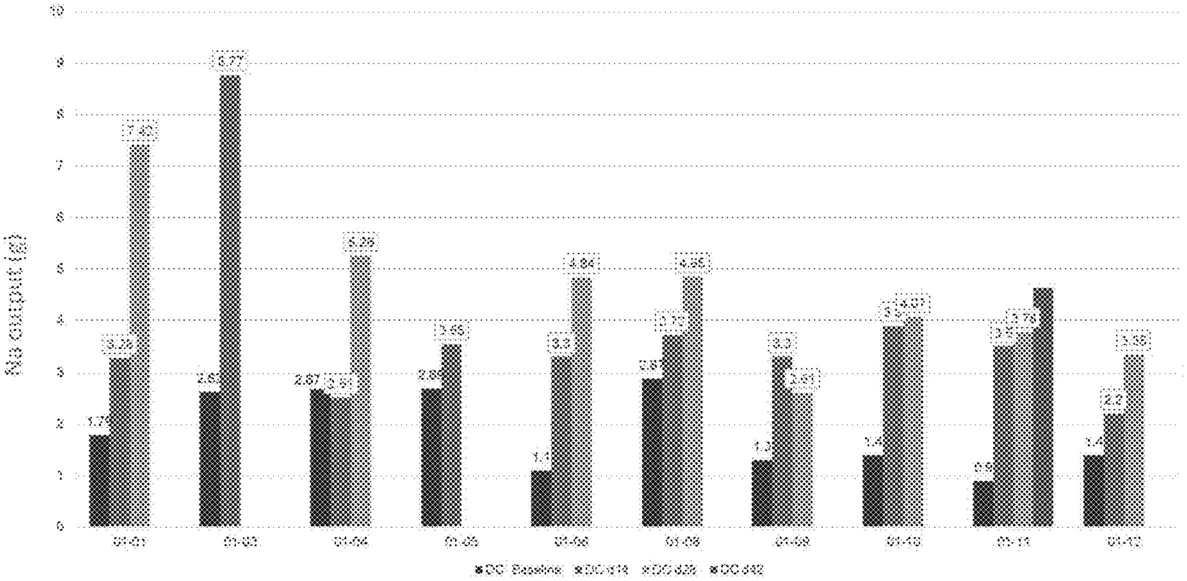
FIG. 5 is a table showing durable reductions in loop diuretics resulting from a third human trial of DSR treatments in heart failure patients with severe fluid overload.
FIG. 6 is chart showing the sodium outputs diuretic challenges conducted at two week intervals after DSR treatments during the third human trial.

FIG. 5 is a table that presents the results of the follow-up period for the patients in the third trial. After several months hiatus after conclusion of the intensive DSR treatments, several patients have begun to take loop diuretics, but in much smaller doses that before they participated in the trial. For example, in the table of FIG. 5, patient 01-01 resumed a dose of 20 mg of furosemide two and half months after the conclusion of the first phase, which was increased to 40 mg after a further 2.5 months. After 15 months since conclusion of the two weeks of intensive DSR treatments, patient 01-01 continues to experience a 90% reduction in furosemide dosage compared to that at the outset of the study. Overall, as shown in FIG. 5, the group of patients experienced reductions of from 67% to 100% in use of loop diuretics, which reduction has been durable up to more than a year after the intensive treatment.

FIG. 6 is a chart showing sodium output data during 6-hour diuretic challenges conducted for the patients in the third trial, at baseline and two week intervals after DSR treatment. Many patients repeated the challenge after four weeks, and one patient repeated the challenge at six weeks. During each diuretic challenge, each patient was administered a dose of 40 mg of furosemide, and sodium output in the patient urine was measured over the following six hours. As indicated in FIG. 6, the sodium output for almost of all patients after the DSR treatments more than doubled from the baseline sodium output.

Based on the results of three human trials discussed above, which employed a single composition of DSR infusate, i.e., sodium-free 10 wt % dextrose, it is theorized that DSR therapy interspersed with a renal failure patient's regularly conducted dialysis sessions may substantially enhance long-term efficacy of loop diuretics, permit the administration of reduced doses, and arrest and possibly reverse renal disease and heart failure. Similarly, for heart failure patients, episodes of DSR therapy can eliminate excess fluid, improve cardiovascular and renal performance and permit reduced or zero doses of loop diuretics for sustained periods following DSR therapy. In particular, DSR therapy may enable a patient's physician to gradually reduce fluid and sodium overload over a period of several weeks to months, and thereby establish an improved sodium and fluid metabolism for the patient that ameliorates either renal failure or heart failure.

Figure 7:
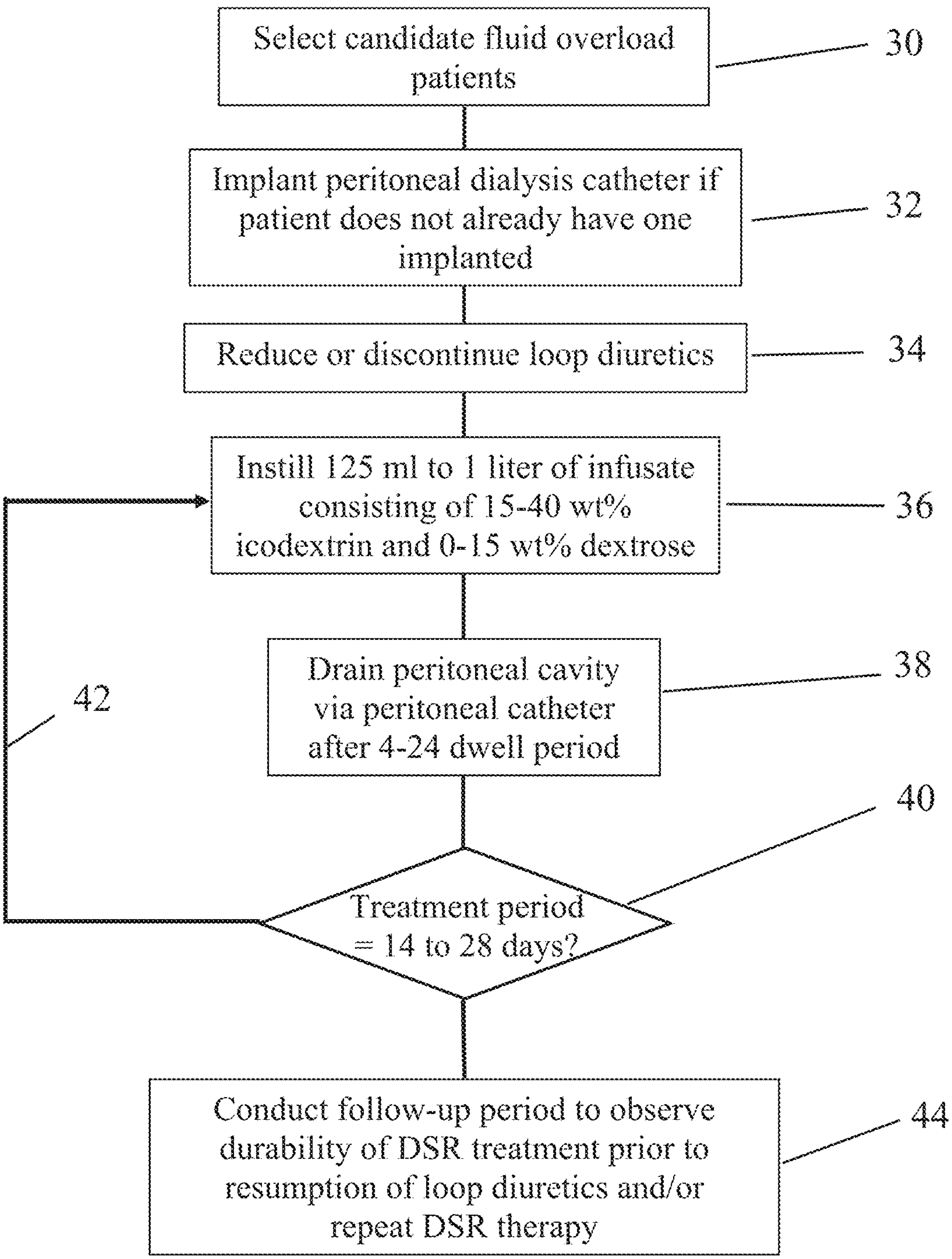
FIG. 7 is an exemplary protocol for treating a patient suffering from fluid overload from renal failure or heart failure.

Turning now to FIG. 7, a method of using a DSR infusate comprising 15-40 wt % icodextrin and 0-15 wt % dextrose, and more preferably 30 wt % icodextrin and 10 wt % dextrose, to treat fluid overload patients, including renal heart failure patients, is described. The method begins at step 30, in which candidate fluid overload patients, such as renal or heart failure patients, are selected for DSR therapy. Inclusion and exclusion criteria for candidates may be as set forth above for the first in human trials. If the patient already has an implanted peritoneal dialysis catheter, that catheter may be used for DSR therapy; if not, a peritoneal dialysis catheter is implanted at step 32. At step 34, the patient's normal regimen of loop diuretics is reduced or suspended, so as not to confound the therapeutic benefits of the DSR therapy.

At step 36, on a first treatment day of a 14 to 28 day treatment period, between 125 ml and 1.0 liter of the DSR infusate is instilled into the patient's peritoneal cavity using the implanted peritoneal dialysis catheter. During a 4 to 24 hour dwell period, the patient may be monitored to confirm the patient does not experience undue discomfort and remains hemodynamically stable. Such monitoring may include verbal interactions with the patient, blood pressure, temperature and pulse rate measurements, and/or a blood sample to confirm serum sodium levels remain stable.

At step 38, after a 4 to 24 hour dwell period, the patient's peritoneal cavity is drained via the peritoneal dialysis catheter. As noted above, applicants' testing has demonstrated that net collected drainage volumes will be multiples of the amount of instilled infusate. The collected fluid also has been observed to be isotonic for sodium, and results in removal of several grams of sodium without significantly reducing blood serum sodium levels. In accordance with this method, at step 40, on a subsequent treatment day during the 14 to 28 day treatment period, which may immediately follow the first treatment day, or follow one, two, three, four, five or six days later, between 125 ml and 1.0 liter of DSR infusate again is instilled in the patient's peritoneal cavity, at steps 42, and steps 36-40 may be repeated. In this manner, the patient may undergo repeated DSR treatments during the 14 to 28 day treatment period. It is hypothesized that by undergoing such repeated processes, the patient's store of extravascular sodium may be depleted, thereby extending the durability of the beneficial effect of the DSR therapy.

At step 44, a follow-up period may be initiated to observe the long-term effect and durability of the DSR therapy. If during the follow-up period the patient begins to accumulate excess fluid, loop diuretics may again be prescribed for the patient at higher doses, and/or DSR treatment may be repeated. During applicants' clinical trials, it was observed that when loop diuretics were reinstituted, the dosages levels were significantly lower than before DSR therapy was begun.

In view of the encouraging results obtained in the three above-described human trials, a further study was conducted using a DSR infusate consisting of sodium-free 30 wt % icodextrin solutions with up to 10 wt % dextrose, and the method described in FIG. 7. This study was designed to evaluate short-term safety and tolerability of sodium-free intraperitoneal 30% icodextrin and 10% dextrose solution in patients with chronic kidney failure undergoing peritoneal dialysis patients. During the study, ten patients had a 500 ml dose of the foregoing DSR infusate instilled into the peritoneal cavity for a 24 hour dwell period. Upon completion of the dwell period, the peritoneal cavity was drained. The study was conducted as an open-label, single-center, exploratory study in patients with chronic kidney disease who previously had peritoneal dialysis catheters implanted.

Inclusion Criteria:

1. Adults over the age of eighteen.
2. Patients with chronic kidney failure under peritoneal dialysis treatment and having a functional peritoneal dialysis catheter.
3. Patient's peritoneal dialysis prescription not changed in previous month (ongoing peritoneal dialysis as an outpatient or ongoing automated peritoneal dialysis).
4. . . . . Signed informed consent.
5. Peritoneal dialysis catheter and the transfer line compatible with the peritoneal dialysis bag (Luer male connector).
6. Patient clinically euvolemic as assessed by treating physician with no change to peritoneal dialysis prescription since performance of a peritoneal equilibrium test.

Exclusion Criteria:

1. Diabetes mellitus, type 1 or uncontrolled type 2 (HbA11c hemoglobin >8%).
2. Active infection or active bleeding.
3. Serum sodium prior to the study <130 mmol/l.
4. Serum bicarbonate prior to the study <18 mmol/l.
5. Peritoneal dialysis prescription using only solutions with 1.5% dextrose (lowest concentration available).
6. Hemoglobin <8 g/dl.
7. Peritoneal dialysis prescription using 4.25% dextrose solution at least once daily.
8. Membrane defect or mechanical defect.
9. Diastolic dysfunction with an increase in filling pressure according to the echocardiogram. (E/A ratio of >2.5 or an E/E ratio of >15).

10. Active or suspected peritonitis as assessed by treating physician.

Study Procedure: The peritoneal dialysis procedure began by connecting a dialysis bag containing the study solution (total volume of 500 ml DSR infusate) to the subject's peritoneal dialysis catheter. The catheter was disconnected and sealed once the total volume was infused. The subjects remained hospitalized during the entire 24 hour dwell time. Peritoneal liquid was sampled every 15 minutes during the first two hours, every 30 minutes during hour 3 and 4 and every hour until end of dwell time. Vital signs (blood pressure heart rate, respiration rate SpO2 and body temperature) were recorded every 30 minutes during the first 4 hours followed by measurements every hour until hour 24. Blood samples for point-of-care analysis were drawn at 3, 6, 12, 18, and 24 hours. Patients were monitored for any signs of adverse events during the entire treatment time.

Patients were given a standard diet containing 3 g of sodium and could consume water and savory snacks as desired to reduce the risk of hypovolemia. They were encouraged to increase liquid intake if point-of-care blood analyses revealed any signs of hypovolemia or given an intravenous Hartmann's solution (Lactated Ringer's Solution). Urine output over the 24 h dwell time was summed-up. Blood samples taken at baseline and at the end of the 24 h dwell time were analyzed for urea, creatinine, glucose, uric acid, magnesium, calcium, phosphorus, bicarbonate and albumin, globulin, total protein, Total bilirubin, alkaline phosphatase, and lactic dehydrogenase. Blood samples taken during dwell time were analyzed immediately using a point-of-care analysis device (Instrumentation Laboratory Gem Premier 3500 Blood Gas Analyzer) for pH, pO2, PCO2, bicarbonate, sodium, potassium and hemoglobin. Primary peritoneal liquid samples labeled with patient identification and timepoint of collection were collected and analyzed offsite for icodextrin, potassium, bicarbonate, sodium, glucose and other analytes.

Upon completion of the 24 hour dwell time, the subjects' peritoneal cavity was drained completely. The patient's weight was measured before and after the drainage. Patients again were asked to empty their bladder and an echocardiogram and bio impedance was performed. Subsequently, patients resumed their regular PD prescriptions (outpatients: immediately; patients with automated PD but without recent infusion: immediately; patients with automatic PD and with recent infusion: until the next scheduled cycle on the same evening).

Demography and baseline characteristics for the group of ten patients that completed the study are set forth in the following below:

| Category | Subjects (n = 10) |
|---|---|
| Age (Year) | |
| Median (Interquartile Range-IQR) | 58 (18) |
| Sex, n (%) | |
| Male | 7 (70) |
| Female | 3 (30) |
| Medical History, n (%) | |
| Diabetes type 2 | 6 (60) |
| Hypertension | 10 (100) |
| Smoker | |
| active | 0 (0) |
| suspended | 4 (40) |
| Hyperlipidemia | 7 (70) |
| Abdominal surgery | 4 (40) |
| Heart Failure | 0 (0) |
| Kidney transplant | 0 (0) |
| Alcohol or illicit drug use | 0 (0) |
| End stage renal disease | |
| Etiology of kidney failure, n (%) | |
| Diabetes Type 2 | 6 (60) |
| Hypertension | 0 (0) |
| Glomerulonephritis | 0 (0) |
| Idiopathic | 3 (30) |
| Other (nephrolithiasis) | 1 (10) |
| Duration of PD requirement (years) | |
| Median (IQR) | 2 (3) |
| Type of PD, n (%) | |
| CAPD | 1 (10) |
| APD | 9 (90) |
| Number of PD bags/day, n (%) | |
| 1 | 0 (0) |
| 2 | 9 (90) |
| 3 | 0 (0) |
| >4 | 1 (10) |

All 10 patients completed the 24-hour dwell and the infusate was well tolerated with mild pain being reported mainly during infusion, thus fulfilling criteria that the infusate was tolerable. Median total drained volume was 3031.5 ml (IQR 528 mL), with a median total of 387 mmol (IQR 62 mmol) of sodium removed. Otal excretion of chloride was lower than that of sodium, which is an advantage of this treatment as compared with loop diuretic therapy where chloride wasting is common further worsening diuretic resistance.

Figure 8:
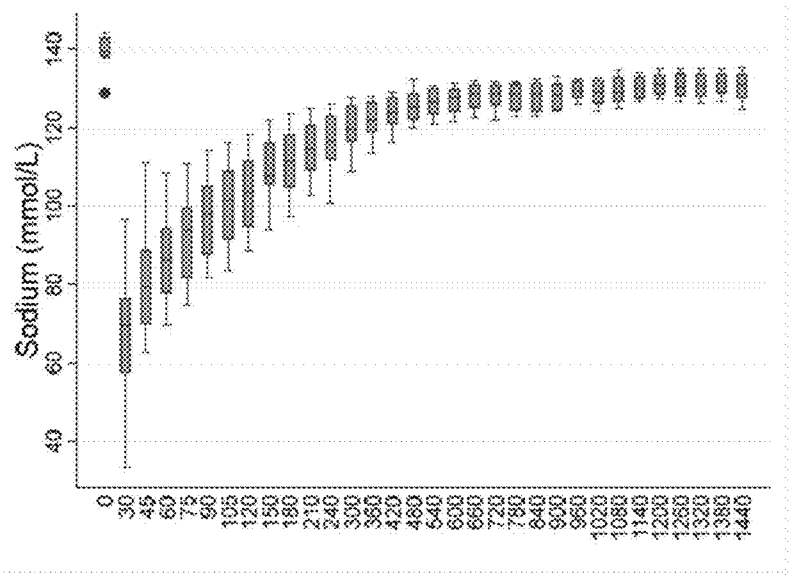
FIGS. 8, 9 and 10 are graphs of sodium, icodextrin and glucose concentrations in the peritoneal fluid at the measurement time points during a fourth study conducted by instilling 500 ml of a no sodium infusate containing 10 wt % dextrose and 30 wt % icodextrin for 24 hours.
Figure 9:
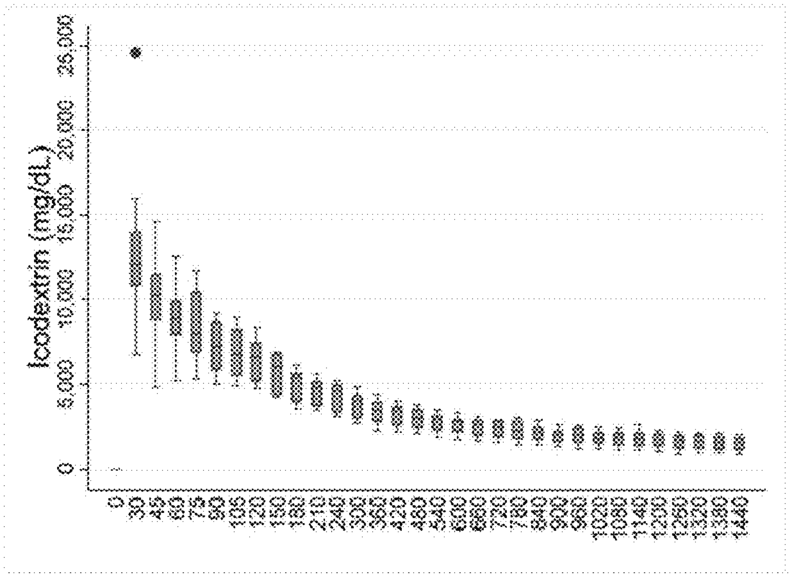
Figure 10:
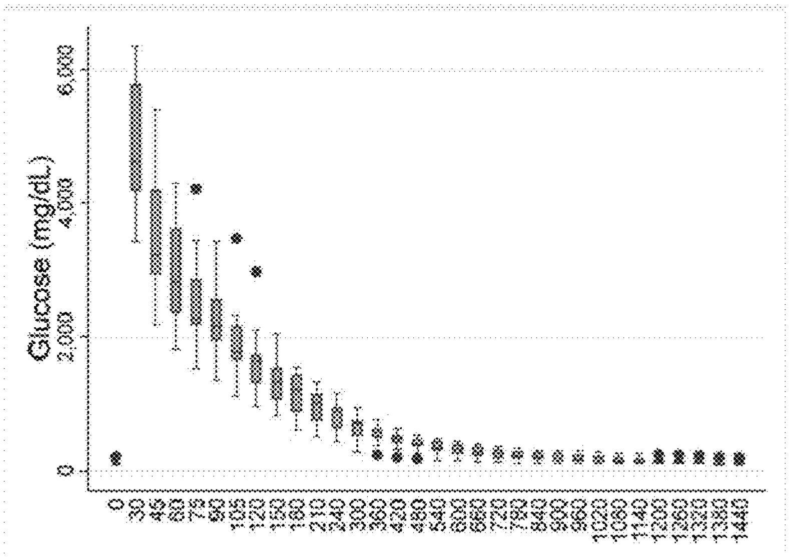

Median sodium concentration in the peritoneal dialysis liquid at the end of the 24-hour dwell time was 130 mmol/L (IQR 6; N=10). Median total amount of sodium removed as calculated by multiplication with the total volume drained from each subject was 387 mmol (IQR 62 mmol). FIGS. 8, 9 and 10 are graphs of sodium, icodextrin and glucose concentrations in the peritoneal fluid at the measurement time points during the study. In particular, FIG. 8 shows that the sodium concentration, rises from zero to about 110 mmol/L within 2 hours of instilling the infusate in the peritoneal cavity. FIG. 9 indicates that the concentration of the icodextrin in the peritoneal fluid declines rapidly in the first 3 hours, than continues slowly declining during the remainder of the dwell period. FIG. 10 also displays a rapid decline after initial instillation, and declines asymptotically towards zero.

Figure 11:
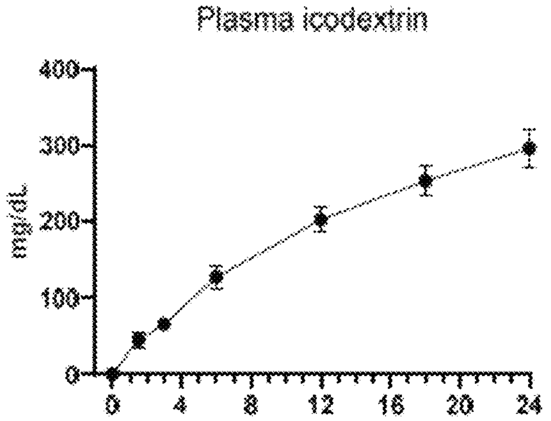
FIGS. 11, 12, 13 and 14 describe the pharmacokinetics of the icodextrin as a function of time during the dwell period for the fourth study.
Figure 12:
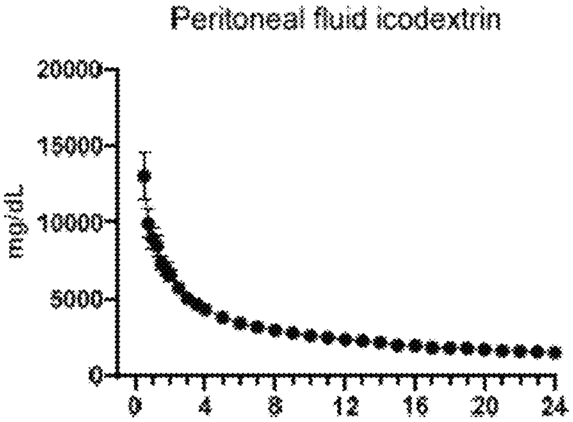
Figure 13:
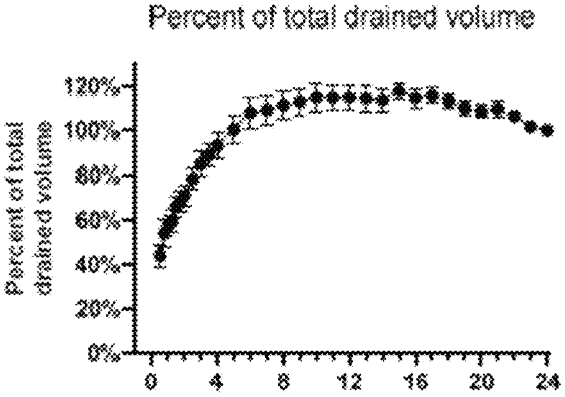
Figure 14:
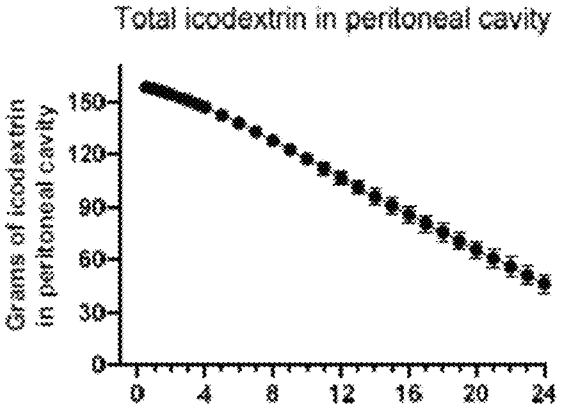

Referring now to FIGS. 11-14, the pharmacokinetics of the icodextrin as a function of time during the dwell period are discussed. Dots are mean values and error bars correspond to standard errors of the mean. In particular, FIG. 11 displays the icodextrin concentration in the patient's plasma; FIG. 12 describes the icodextrin concentration in peritoneal dialysis fluid; FIG. 13 displays the estimated percent of drained volume; and FIG. 14 corresponds to the estimated total amount of icodextrin present in the peritoneal cavity. Peritoneal volumes utilized for FIGS. 13 and 14 were computed by assuming a linear loss of fluid from the peritoneal fluid cavity to account for the measured absorption of icodextrin (total mass of icodextrin infused vs. total mass of icodextrin recovered in the drain). In all cases, the abscissa represents hours of dwell time.

FIGS. 11 and 12, taken together, demonstrate an unexpected advantage of using a high concentration of icodextrin in a relatively small (500 ml) of infusate that also includes dextrose. Specifically, the rapid decrease in icodextrin concentration in the peritoneal fluid, as shown in FIG. 12, compared to the relatively steady rise in icodextrin concentration in plasma results from the rapid influx of ultrafiltrate into the peritoneal cavity shortly after the DSR infusate is instilled. This is consistent with the rapid absorption of glucose (see FIG. 10) across the peritoneal membrane, while the bulk of the icodextrin remains in the peritoneal cavity but its concentration drops due to dilution caused by the influx of water.

More specifically, it was observed that dextrose quickly is absorbed across the peritoneal membrane into the body primarily via diffusion. As a result, the clearance of dextrose is directly proportional to the concentration of glucose as such diffusion will increase proportionately to the concentration gradient. Because the peritoneal membrane is not permeable to icodextrin, clearance of icodextrin from the peritoneal cavity occurs primarily via pumping of peritoneal fluid at a continuous rate by the lymphatic system (e.g., 50-100 ml/hour of fluid). While clearance of large volumes of dilute icodextrin (e.g., 2 L of 7.5% icodextrin) would be very slow, the use of small volumes of infusate having a high concentration of icodextrin would be disadvantageous. This would be so because the fluid removed by the lymphatics system shortly after instillation would have a very high concentration of icodextrin (e.g., 100 ml of 30% icodextrin contains much more icodextrin than 100 ml of 7.5% icodextrin).

To counteract this effect, it was observed that inclusion of a fast acting osmotic agent, such as dextrose, in the high concentration icodextrin infusate provides a number of important advantages, With the addition of 10 wt % dextrose, when 500 ml of the above-described infusate is instilled into the peritoneum, the dextrose component, due to its osmotic properties, quickly drags water and sodium into the abdominal cavity before it migrates through the peritoneal wall and is metabolized. This results in rapid dilution of icodextrin, by up to four times, such that the icodextrin remaining in the peritoneal cavity starts pulls water and sodium by its oncotic forces. Accordingly, 500 ml of 30 wt % icodextrin infusate expands rapidly to a larger volume of fluid, such that the rate at which icodextrin is removed by the lymphatic system is greatly reduced.

By comparison, use of a dilute icodextrin solution, e.g., 7.5 wt %, would require instillation of a much larger volume of fluid to prevent the rapid absorption issue noted above. Moreover, instillation of a large volume of low or no sodium infusate may promptly cause hyponatremia by drawing a large amount of sodium to the peritoneum, without a corresponding amount of free water. While providing a higher sodium concentration in a dilute icodextrin infusate would reduce the risk of hyponatremia, it also would reduce the efficacy of the DSR treatment with respect to sodium removal.

The fourth study was conducted with a no sodium infusate. However, it is theorized that a 30 wt % icodextrin/10 wt % dextrose infusate could be as much as isotonic for sodium (i.e., have sodium concentration of about 132 mmol/l) and still retain the majority of its efficacy in removing excess water. This is so because the solution produces such a powerful ultrafiltration effect (increasing volume about fivefold), of which only about 20% of the efficacy is driven by sodium diffusion vs. convective forces with ultrafiltration.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of conducting direct sodium removal (DSR) therapy for a patient, the method comprising:
- providing an infusate comprising an aqueous solution of 30 wt % icodextrin and 10 wt % dextrose;
- instilling 250 ml to 750 ml of the infusate into a peritoneal cavity of the patient;
- retaining the infusate in the peritoneal cavity for a 4-24 hour dwell period to induce sodium and ultrafiltrate to accumulate within the peritoneal cavity; and
- removing the infusate, sodium and ultrafiltrate from the peritoneal cavity.

2. The method of claim 1, further comprising, prior to instilling the infusate, reducing or suspending administration of loop diuretics to the patient as compared to the patient's loop diuretic regimen prior to the treatment.

3. The method of claim 1, further comprising, following removal of the infusate, sodium and ultrafiltrate from the peritoneal cavity, reducing or suspending administration of loop diuretics to the patient during a follow-up period of at least three months as compared to the patient's loop diuretic regimen prior to the treatment.

4. The method of claim 1, wherein the infusate is instilled into the peritoneal cavity using a peritoneal dialysis catheter.

5. The method of claim 4, wherein removal of the infusate, sodium and ultrafiltrate from the peritoneal cavity following the 4-24 hour dwell period uses the peritoneal dialysis catheter.

6. The method of claim 4, wherein removal of the infusate, sodium and ultrafiltrate from the peritoneal cavity following the 4-24 hour dwell period uses an implantable pump to transfer fluid from the peritoneal cavity to a bladder of the patient.

7. The method of claim 1, wherein the infusate is instilled into the peritoneal cavity via a subcutaneous port.

8. The method of claim 7, wherein removal of the infusate, sodium and ultrafiltrate from the peritoneal cavity following the 4-24 hour dwell period uses an implantable pump to transfer fluid from the peritoneal cavity to a bladder of the patient.

9. The method of claim 1, wherein providing the infusate further comprises providing an infusate having a sodium concentration lower than 135 meq/l.

10. The method of claim 1, wherein the dextrose rapidly crosses a peritoneal membrane of the patient and draws water into the peritoneal cavity to dilute the concentration of icodextrin, thereby reducing a rate at which the icodextrin is removed from the peritoneal cavity.

11. A method of conducting direct sodium removal (DSR) therapy for a patient, the method comprising:
- providing an infusate comprising an aqueous solution of 30 wt % icodextrin and 10 wt % dextrose;
- during a 14-28 day treatment period, on a first treatment day, instilling between 250 ml and 750 ml of the infusate into a peritoneal cavity of the patient;
- retaining the infusate in the peritoneal cavity for a first 4-24 hour dwell period to induce sodium and ultrafiltrate to accumulate within the peritoneal cavity;
- removing the infusate, sodium and ultrafiltrate from the peritoneal cavity;

during subsequent treatment days, up to once daily following the first treatment day, instilling between between 250 ml and 750 ml of the infusate into the peritoneal cavity of the patient;

retaining the infusate in the peritoneal cavity for subsequent 4-24 hour dwell periods during subsequent treatment days to induce sodium and ultrafiltrate to accumulate within the peritoneal cavity; and removing the infusate, sodium and ultrafiltrate from the peritoneal cavity.

12. The method of claim 11, further comprising, prior to the first treatment day, reducing or suspending administration of loop diuretics to the patient as compared to the patient's loop diuretic regimen prior to the treatment.

13. The method of claim 11, further comprising, following the 14-28 day treatment period removal, reducing or suspending administration of loop diuretics to the patient during a follow-up period of at least three months as compared to the patient's loop diuretic regimen prior to the treatment.

14. The method of claim 11, wherein the infusate is instilled into the peritoneal cavity using a peritoneal dialysis catheter.

15. The method of claim 14, wherein removal of the infusate, sodium and ultrafiltrate from the peritoneal cavity following the first and subsequent 4-24 hour dwell period uses the peritoneal dialysis catheter.

16. The method of claim 14, wherein removal of the infusate, sodium and ultrafiltrate from the peritoneal cavity following the first and subsequent dwell periods uses an implantable pump to transfer fluid from the peritoneal cavity to a bladder of the patient.

17. The method of claim 11, wherein the infusate is instilled into the peritoneal cavity via a subcutaneous port.

18. The method of claim 17, wherein removal of the infusate, sodium and ultrafiltrate from the peritoneal cavity following the first and subsequent 4-24 hour dwell periods uses an implantable pump to transfer fluid from the peritoneal cavity to a bladder of the patient.

19. The method of claim 11, wherein providing the infusate further comprises providing an infusate having a sodium concentration lower than 135 meq/l.

20. The method of claim 11, wherein the dextrose rapidly crosses a peritoneal membrane of the patient and draws water into the peritoneal cavity to dilute the concentration of icodextrin, thereby reducing a rate at which the icodextrin is removed from the peritoneal cavity.

* * * * *